US007680537B2

(12) United States Patent
Stahmann et al.

(10) Patent No.: US 7,680,537 B2
(45) Date of Patent: *Mar. 16, 2010

(54) THERAPY TRIGGERED BY PREDICTION OF DISORDERED BREATHING

(75) Inventors: Jeffrey E. Stahmann, Ramsey, MN (US); John D. Hatlestad, Maplewood, MN (US); Quan Ni, Shoreview, MN (US); Jesse Hartley, Lino Lakes, MN (US); Douglas R. Daum, Oakdale, MN (US); Kent Lee, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 852 days.

This patent is subject to a terminal disclaimer.

(21) Appl. No.: 10/643,154

(22) Filed: Aug. 18, 2003

(65) Prior Publication Data

US 2005/0043772 A1 Feb. 24, 2005

(51) Int. Cl.
*A61N 1/18* (2006.01)
(52) U.S. Cl. ...................................................... 607/42
(58) Field of Classification Search .................. 607/42; 600/481–543
See application file for complete search history.

(56) References Cited

U.S. PATENT DOCUMENTS

| | | | | |
|---|---|---|---|---|
| 4,365,636 A | * | 12/1982 | Barker | .......................... 600/529 |
| 4,702,253 A | | 10/1987 | Nappholz et al. | |
| 5,105,354 A | | 4/1992 | Nishimura | |
| 5,335,657 A | * | 8/1994 | Terry et al. | .................... 607/45 |
| 5,466,245 A | | 11/1995 | Heemels et al. | |
| 5,645,570 A | | 7/1997 | Corbucci | |
| 5,738,102 A | | 4/1998 | Lemelson | |
| 5,970,975 A | | 10/1999 | Estes et al. | |
| 6,064,910 A | | 5/2000 | Andersson et al. | |
| 6,126,611 A | * | 10/2000 | Bourgeois et al. | ........... 600/529 |
| 6,270,457 B1 | | 8/2001 | Bardy | |
| 6,272,377 B1 | * | 8/2001 | Sweeney et al. | ............. 600/515 |
| 6,312,378 B1 | | 11/2001 | Bardy | |
| 6,336,903 B1 | | 1/2002 | Bardy | |
| 6,366,813 B1 | * | 4/2002 | DiLorenzo | .................... 607/45 |
| 6,398,728 B1 | * | 6/2002 | Bardy | ......................... 600/300 |
| 6,415,183 B1 | | 7/2002 | Scheiner et al. | |

(Continued)

FOREIGN PATENT DOCUMENTS

EP  1 172 125 A1  1/2002

OTHER PUBLICATIONS

Waldemark, Katrina et al., Detection of Apnea Using Short Window FFT Technique and Artificial Neural Network, SPIE, International Society for Optical Engineering, vol. 3390, pp. 122-133 (1998).

(Continued)

*Primary Examiner*—George R Evanisko
*Assistant Examiner*—Alyssa M Alter
(74) *Attorney, Agent, or Firm*—Hollingsworth & Funk, LLC

(57) ABSTRACT

An approach to providing disordered breathing therapy includes providing therapy based on a prediction of disordered breathing. One or more patient conditions are detected and used to predict disordered breathing. Therapy is delivered to mitigate the predicted disordered breathing. The disordered breathing therapy may be adapted to enhance therapy efficacy and/or to reduce the impact of the therapy to the patient.

69 Claims, 23 Drawing Sheets

U.S. PATENT DOCUMENTS

| | | |
|---|---|---|
| 6,574,507 B1 | 6/2003 | Bonnet |
| 6,580,944 B1 | 6/2003 | Katz et al. |
| 6,641,542 B2 | 11/2003 | Cho et al. |
| 6,741,885 B1 | 5/2004 | Park et al. |
| 6,928,324 B2 * | 8/2005 | Park et al. ............... 607/20 |
| 6,964,641 B2 | 11/2005 | Cho et al. |
| 7,155,278 B2 | 12/2006 | King et al. |
| 7,225,013 B2 | 5/2007 | Geva et al. |
| 2002/0193697 A1 * | 12/2002 | Cho et al. .............. 600/529 |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0216789 A1 | 11/2003 | Deem et al. |
| 2004/0002742 A1 | 1/2004 | Florio |
| 2004/0030362 A1 | 2/2004 | Hill et al. |
| 2004/0116981 A1 | 6/2004 | Mazar |
| 2004/0122488 A1 | 6/2004 | Mazar et al. |
| 2004/0128161 A1 | 7/2004 | Mazar et al. |
| 2004/0133079 A1 | 7/2004 | Mazar et al. |
| 2005/0039745 A1 * | 2/2005 | Stahmann et al. ...... 128/204.18 |
| 2005/0042589 A1 * | 2/2005 | Hatlestad et al. ............ 434/262 |
| 2005/0043644 A1 * | 2/2005 | Stahmann et al. ........... 600/529 |
| 2005/0043772 A1 | 2/2005 | Stahmann et al. |

OTHER PUBLICATIONS

U.S. Appl. No. 10/269,611, filed Oct. 11, 2002, Hatlestad.
U.S. Appl. No. 10/309,770, filed Dec. 4, 2002, Ni et al.
U.S. Appl. No. 10/309,771, filed Dec. 4, 2002, Ni et al.
U.S. Appl. No. 10/642,998, filed Aug. 18, 2003, Hatlestad et al.
U.S. Appl. No. 10/643,203, filed Aug. 18, 2003, Stahmann et al.
U.S. Appl. No. 10/643,006, filed Aug. 18, 2004, Lovett et al.
Office Action dated Jun. 29, 2007 from co-pending U.S. Appl. No. 10/643,016, filed Aug. 18, 2003.

* cited by examiner

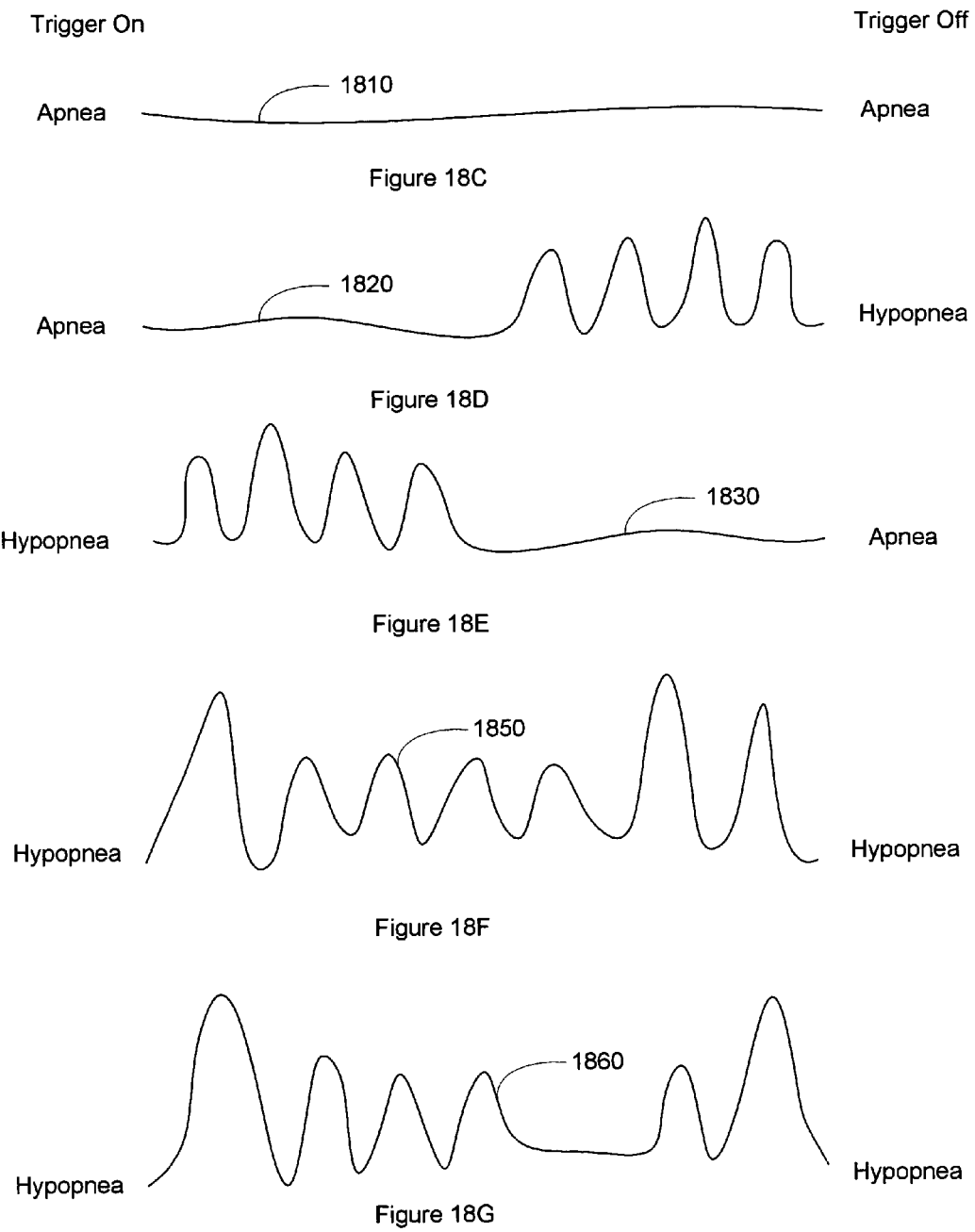

THERAPY TRIGGERED BY PREDICTION OF DISORDERED BREATHING

FIELD OF THE INVENTION

The present invention relates generally to providing therapy for disordered breathing based on prediction of disordered breathing.

BACKGROUND OF THE INVENTION

Disordered breathing refers to a wide spectrum of respiratory conditions that involve disruption of the normal respiratory cycle. Although disordered breathing typically occurs during sleep, the condition may also occur while the patient is awake. Respiratory disruption can be particularly serious for patients concurrently suffering from cardiovascular deficiencies, such as congestive heart failure. Unfortunately, disordered breathing is often undiagnosed. If left untreated, the effects of disordered breathing may result in serious health consequences for the patient.

Various types of disordered respiration have been identified, including, for example, apnea, hypopnea, dyspnea, hyperpnea, tachypnea, and periodic breathing, including Cheyne-Stokes respiration (CSR). Apnea is a fairly common disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer.

In addition to apnea, other types of disordered respiration have been identified, including hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes breathing. Periodic breathing is characterized by cyclic respiratory patterns that may exhibit rhythmic rises and falls in tidal volume. Cheyne-Stokes respiration is a specific form of periodic breathing wherein the tidal volume decreases to zero resulting in apneic intervals. The breathing interruptions of periodic breathing and CSR may be associated with central apnea, or may be obstructive in nature. CSR is frequently observed in patients with congestive heart failure (CHF) and is associated with an increased risk of accelerated CHF progression. Because of the cardiovascular implications, therapy for respiration-related sleep disorders is of particular interest.

SUMMARY OF THE INVENTION

Various embodiments of present invention involve methods and systems for providing disordered breathing therapy based on prediction of disordered breathing.

In accordance with an embodiment of the invention, a method of providing therapy for disordered breathing involves detecting one or more conditions associated with disordered breathing and predicting disordered breathing based on the one or more detected conditions. Therapy to mitigate the predicted disordered breathing is delivered. At least one of detecting the conditions, predicting the disordered breathing, and delivering the therapy is performed at least in part implantably.

In accordance with a further embodiment of the invention, a method of providing disordered breathing therapy involves predicting disordered breathing and adapting a therapy to mitigate the disordered breathing. The adapted therapy is delivered to the patient. At least one of predicting the disordered breathing, adapting the therapy, and delivering the adapted therapy is performed at least in part implantably.

Yet another embodiment of the invention includes a medical device for providing disordered breathing therapy. The medical device includes a detector system configured to detect one or more conditions associated with disordered breathing. A prediction engine is coupled to the detector system and is configured to predict disordered breathing based on the one or more detected conditions. A therapy delivery system is coupled to the prediction engine and is configured to delivery therapy to the patient to mitigate the predicted disordered breathing.

A further embodiment of the invention involves a disordered breathing therapy system including means for detecting one or more conditions associated with disordered breathing and means for predicting disordered breathing based on the detected conditions. The system further includes means for delivering therapy to mitigate the predicted disordered breathing. At least one of the means for detecting the one more conditions, the means for predicting disordered breathing, and the means for delivering therapy includes an implantable component.

Yet another embodiment of the invention involves a system for providing therapy for disordered breathing. The system includes means for predicting disordered breathing and means for adapting a therapy to mitigate the predicted disordered breathing. The system further includes means for delivering the adapted therapy to the patient. At least one of the means for predicting disordered breathing, the means for adapting a therapy to mitigate the disordered breathing, and the means for delivering the adapted therapy to the patient includes an implantable component.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 18C-18G are graphs illustrating disordered breathing events comprising a mixture of apnea and hypopnea respiration cycles;

Figure 1:
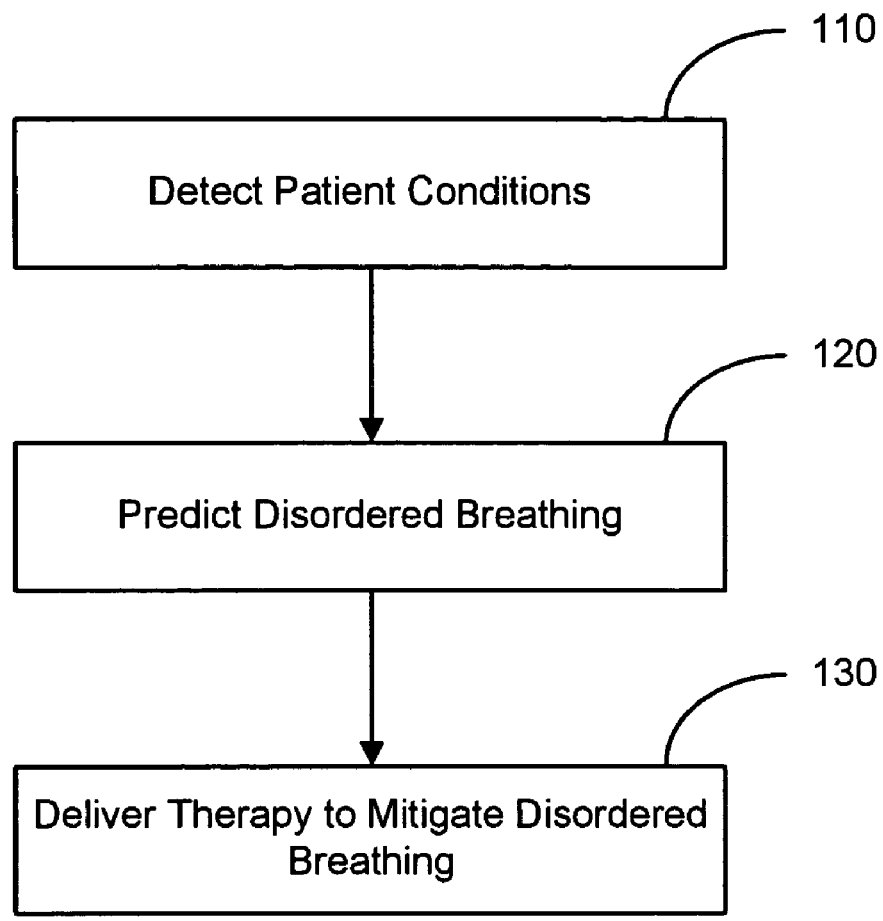
FIG. 1 is a flow graph illustrating a method for providing disordered breathing therapy in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

A significant percentage of patients between the ages of 30 and 60 years experience some symptoms of disordered breathing. Sleep disordered breathing is associated with excessive daytime sleepiness, systemic hypertension, increased risk of stroke, angina and myocardial infarction. Disordered breathing is particularly prevalent among congestive heart failure patients, and may contribute to the progression of heart failure.

Various therapies have been used to treat central and/or obstructive disordered breathing episodes. Obstructive sleep apnea has been associated with prolapse of the tongue and its surrounding structure into the pharynx, thus occluding the respiratory pathway. A commonly prescribed treatment for obstructive apnea is continuous positive airway pressure (CPAP). A CPAP device delivers air pressure through a nasal mask worn by the patient. The application of continuous positive airway pressure keeps the patient's throat open, reducing or eliminating the obstruction causing apnea.

Prolapse of the tongue muscles has been attributed to diminishing neuromuscular activity of the upper airway. A treatment for obstructive sleep apnea involves compensating for the decreased muscle activity by electrical activation of the tongue muscles. The hypoglossal (HG) nerve innervates the protrusor and retractor tongue muscles. An appropriately applied electrical stimulation to the hypoglossal nerve, for example, prevents backward movement of the tongue, thus preventing the tongue from obstructing the airway.

Cardiac stimulation may be used as a therapy for disordered breathing. Therapy methods using cardiac pacing is described in commonly owned U.S. patent application Ser. No. 10/643,203 filed Aug. 18, 2003 entitled "Adaptive Therapy for Disordered Breathing," now U.S. Publication No. 2005/0039745, filed concurrently with this patent application, and incorporated by reference herein in its entirety. The cardiac pacing method described uses an adaptive therapy based on detection of disordered breathing. Such a disordered breathing therapy may be adapted, for example, to achieve an overall level of therapy efficacy, patient comfort, sleep quality, interaction with other patient therapies, or device service life.

Embodiments of the invention discussed herein relate to systems and methods providing an adaptive therapy for disordered breathing based on prediction of disordered breathing. Various approaches for predicting disordered breathing are described in commonly owned U.S. patent application Ser. No. 10/643,016 filed Aug. 18, 2003 entitled "Prediction of Disordered Breathing,", now U.S. Pat. No. 7,396,333, filed concurrently with this patent application, and incorporated by reference herein in its entirety.

The flowchart of FIG. 1 illustrates a method for triggering disordered breathing therapy based on a prediction of disordered breathing according to various embodiments of the invention. The method involves detecting 110 conditions associated with disordered breathing and predicting disordered breathing 120 based on the detected conditions. Disordered breathing may be predicted, for example, by comparing the detected conditions to disordered breathing prediction criteria. A representative set of conditions that may be used to predict disordered breathing are listed in Table 1. The representative set of conditions listed in Table 1 is not exhaustive, and conditions other than those listed may be used to predict disordered breathing. If disordered breathing is predicted, therapy is delivered 130 to mitigate the disordered breathing, e.g., reduce the severity of the disordered breathing or prevent the disordered breathing from occurring. One or more of detecting the patient conditions, predicting the disordered breathing based on the detected patient conditions and delivering the therapy to mitigate the disordered breathing is performed as least in part implantably. Implantably performing an operation comprises performing the operation by a process that is performed at least partially within the patient's body, or by using a component, device, or system that is implantable within the patient's body.

Patient conditions used in the disordered breathing prediction may be physiological or contextual (e.g. non-physiological). The physiological conditions may include a broad category of conditions associated with the internal physiological conditions of the patient. Physiological conditions may be further subdivided, for example, into conditions of the cardiovascular, respiratory, and nervous systems, as well as conditions relating to the blood chemistry of the patient. In connection with the prediction of sleep disordered breathing, an additional physiological category associated with the patient's sleep quality may also be defined.

Contextual conditions generally encompass the external conditions affecting the patient. Contextual conditions may be broadly defined to include, for example, non-physiological environmental conditions such as temperature, humidity, air pollution index, ambient noise, and barometric pressure as well as body-related conditions such as patient location, posture, and altitude. Contextual conditions may also include historical conditions relating to the patient, including the patient's normal sleep time and the patient's medical history, for example. Methods and systems for detecting contextual conditions are described in commonly owned U.S. Patent Application identified by Ser. No. 10/269,611, filed Oct. 11, 2002, now U.S. Pat. No. 7,400,928, and incorporated by reference herein in its entirety. Methods and systems for REM sleep detection are described in commonly owned U.S. patent application Ser. No. 10/643,006 filed Aug. 18, 2003 entitled "Sleep State Classification,", now U.S. Publication No. 2005/0043652, filed concurrently with this application and incorporated herein by reference.

Table 1 provides a representative set of patient conditions that may be used in connection with prediction of disordered breathing, along with example sensing methods that may be employed to detect the conditions.

TABLE 1

| Condition Type | | Condition | Sensor type or Detection method |
|---|---|---|---|
| Physiological | Cardiovascular System | Heart rate | EGM, ECG |
| | | Heart rate variability | |
| | | QT interval | |
| | | Ventricular filling pressure | Intracardiac pressure sensor |
| | | Blood pressure | Blood pressure sensor |
| | Respiratory System | Snoring | Accelerometer |
| | | | Microphone |
| | | Respiration pattern (Tidal volume Minute ventilation Respiratory rate) | Transthoracic impedance sensor (AC) |
| | | Patency of upper airway | Intrathoracic impedance sensor |
| | | Pulmonary congestion | Transthoracic impedance sensor (DC) |
| | Nervous System | Sympathetic nerve activity | Muscle sympathetic nerve Activity sensor |
| | | Brain activity | EEG |
| | Blood Chemistry | $CO_2$ saturation | Blood analysis |
| | | $O_2$ saturation | |
| | | Blood alcohol content | |
| | | Adrenalin | |
| | | B-type Natriutetic Peptide (BNP) | |
| | | C-Reactive Protein | |
| | | Drug/Medication/Tobacco use | |
| | Muscle System | Muscle atonia | EMG sensor |
| | | Eye movement | EOG sensor |
| | | Patient activity | Accelerometer, MV, etc. |
| | | Limb movements | Accelerometer |
| | | Jaw movements | EMG sensor |
| Contextual | Environmental | Ambient temperature | Thermometer |
| | | Humidity | Hygrometer |
| | | Pollution | Air quality website |
| | | Time | Clock |
| | | Barometric pressure | Barometer |
| | | Ambient noise | Microphone |
| | | Ambient light | Photodetector |
| | Body-related | Posture | Posture sensor |
| | | Altitude | Altimeter |
| | | Location | GPS, proximity sensor |
| | | Proximity to bed | Proximity to bed sensor |
| | Historical/Background | Historical sleep time | Patient input, previously detected sleep onset times |
| | | Medical history | Patient input device |
| | | Age | |
| | | Recent exercise | |
| | | Weight | |
| | | Gender | |

TABLE 1-continued

| Condition Type | Condition | Sensor type or Detection method |
|---|---|---|
| | Body mass index | |
| | Neck size | |
| | Emotional state | |
| | Psychological history | |
| | Daytime sleepiness | |
| | Patient perception of sleep quality | |
| | Drug, alcohol, nicotine use | |

Episodes of disordered breathing are associated with acute physiological effects, including, for example, negative intrathoracic pressure, hypoxia, and arousal from sleep. During obstructive apnea, for example, the effort to generate airflow increases. Attempted inspiration in the presence of an occluded airway result in an abrupt reduction in intrathoracic pressure. The repeated futile inspiratory efforts associated with obstructive sleep apnea may trigger a series of secondary responses, including mechanical, hemodynamic, chemical, neural, and inflammatory responses.

Obstructive sleep apneas are terminated by arousal from sleep several seconds after the apneic peak, allowing the resumption of airflow. Coincident with arousal from sleep, surges in sympathetic nerve activity, blood pressure, and heart rate occur. The adverse effects of obstructive apnea are not confined to sleep. Daytime sympathetic nerve activity and systemic blood pressure are increased. There may also be a sustained reduction in vagal tone, causing reduction in total heart rate variability during periods of wakefulness.

Central sleep apnea is generally caused by a failure of respiratory control signals from the brain and is a component of Cheyne-Stokes respiration (CSR), a respiration pattern primarily observed in patients suffering from chronic heart failure (CHF). Cheyne-Stokes respiration is a form of periodic breathing in which central apneas and hypopneas alternate with periods of hyperventilation causing a waxing-waning pattern of tidal volume. In some patients, obstructive sleep apnea and central sleep apnea may coexist. In these patients, there is generally a gradual shift from predominantly obstructive apneas at the beginning of the night to predominantly central apneas at the end of the night.

When CHF patients lie down, the prone posture may create central fluid accumulation and pulmonary congestion causing the patient to reflexively hyperventilate. Central apnea is usually initiated during sleep by an increase in ventilation and a reduction of arterial partial pressure of carbon dioxide ($PaCO_2$) that is triggered by spontaneous arousal. When $PaCO_2$ falls below the threshold level required to stimulate breathing, the central drive to the respiratory muscles and airflow cease, and central apnea ensues. Apnea persists until $PaCO_2$ rises above the threshold required to stimulate ventilation.

Arousals are not required in central sleep apneas for the resumption of breathing at the termination of the apneic event. In central apnea, the arousals follow the initiation of breathing and facilitate the development of oscillations in ventilation by recurrently stimulating hyperventilation and reducing $PaCO_2$ below the apneic threshold. Once triggered, the pattern of alternating hyperventilation and apnea is sustained by the combination of increased respiratory drive, pulmonary congestion, arousals, and apnea-induced hypoxia causing $PaCO_2$ oscillations above and below the apneic threshold. Shifts in the patient's state of consciousness, particularly with repeated arousals, may further destabilize breathing.

With the transition from wakefulness to NREM sleep the waking neural drive to breathe is lost, and the threshold for a ventilatory response to $CO_2$ is increased. Therefore, if the patient's $PaCO_2$ level during wakefulness is below this higher sleeping threshold, the transition to NREM sleep may be accompanied by a transient loss of respiratory drive resulting in a central apnea. During the apnea, the $PaCO_2$ rises until it reaches the new higher threshold level and initiates breathing. If sleep becomes firmly established, regular breathing resumes. However, if an arousal should occur, the increased $PaCO_2$ level associated with sleep is now relatively too high for a state of wakefulness and will stimulate hyperventilation. Thus, although arousals terminate obstructive sleep apneas, arousals trigger the respiratory oscillations associated with central apneas, particularly Cheyne-Stokes respiration.

In addition to the acute responses to central sleep apnea discussed above, central sleep apnea is also associated with a number of secondary responses, including, for example, decreased HRV, and blood pressure changes. Patients with central sleep apnea may have higher urinary and circulating norepinephrine concentrations and lower $PaCO_2$ during both sleep and wakefulness.

Figure 2:
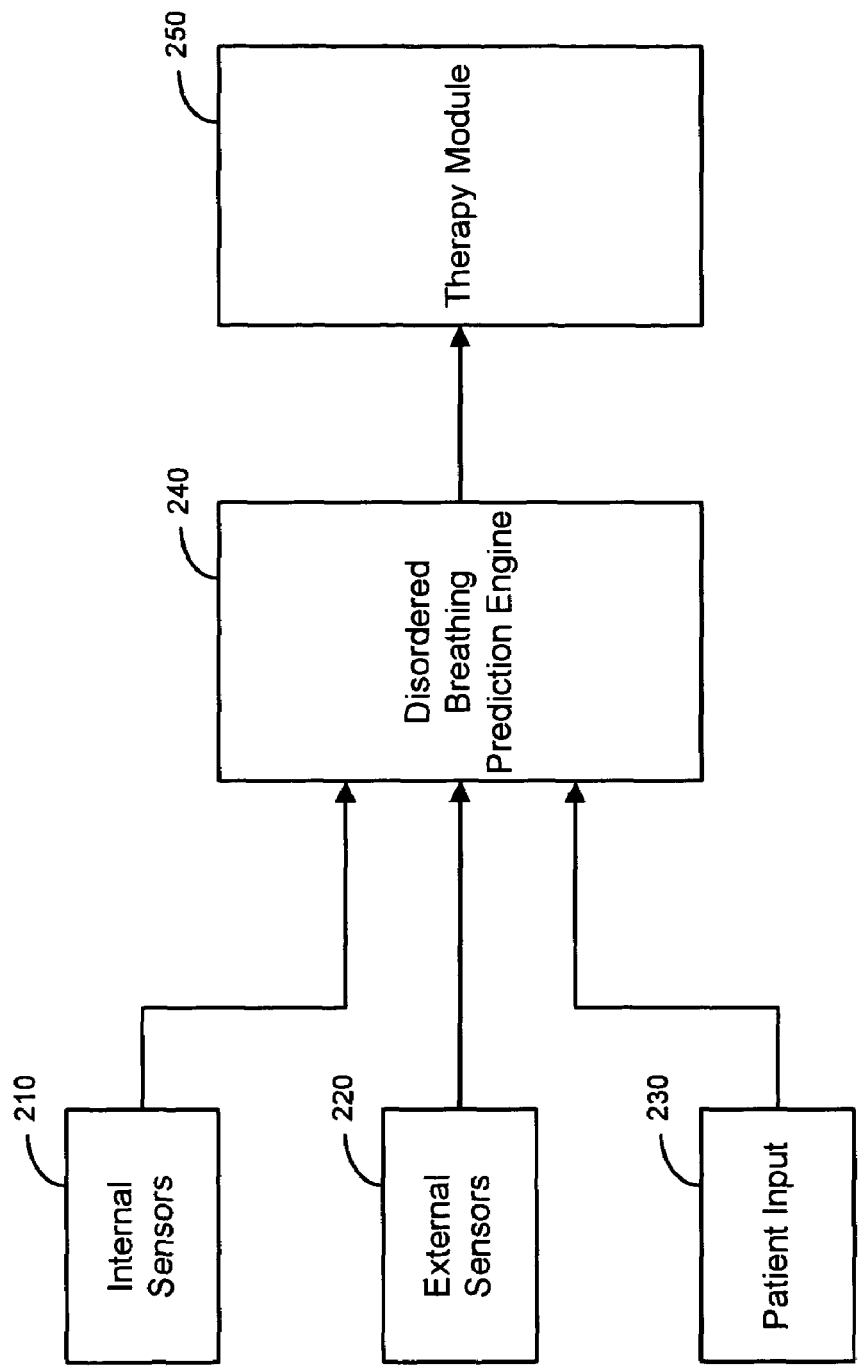
FIG. 2 is a block diagram of a disordered breathing therapy system in accordance with embodiments of the invention.

FIG. 2 illustrates a block diagram of a disordered breathing therapy system configured in accordance with embodiments of the invention. It is understood that configurations, features, and combinations of features described herein can be implemented in a wide range of medical devices, and that such embodiments and features are not limited to the particular devices described herein.

The system may use patient-internal sensors 210, implanted within the body of the patient, to detect physiological conditions. For example, the system may determine heart rate, heart rate variability, respiration cycles, tidal volume, and/or other physiological signals using an intracardiac electrocardiogram (EGM) signal detector and transthoracic impedance sensor that are part of an implanted cardiac rhythm management system such as a cardiac pacemaker or defibrillator.

The system may use patient-external sensors 220 to detect physiological or contextual conditions. In one scenario, whether the patient is snoring may be useful in predicting disordered breathing. Snoring may be detected using an external microphone or an implanted accelerometer. In another situation, temperature and humidity may be factors in the patient's disordered breathing. Signals from temperature and humidity sensors may be used to aid in the prediction of disordered breathing.

Additionally, the system may use information input 230 by the patient to inform the disordered breathing prediction system of one or more patient conditions. In various embodiments, the patient's medical history, self-described medication use, alcohol or tobacco use, day-time sleepiness, or perceptions of sleep quality over the past one or more sleep periods may be useful in connection with the disordered breathing prediction.

Signals from one or more of the patient-internal sensors 210, patient-external sensors 220, and patient input devices 230 may be coupled to a disordered breathing prediction engine 240 for prediction evaluation. In one implementation, the prediction engine 240 may compare the patient conditions to one or more sets of disordered breathing criteria and predict disordered breathing based on the comparison. The prediction engine 240 is coupled to a therapy module 250. If disordered breathing is predicted, the therapy module 250 delivers an appropriate therapy to the patient to mitigate the disordered breathing.

In one example, the patient conditions may be sensed and processed using implantable sensors 210, and the prediction analysis and therapy delivery may be performed by a patient-external disordered breathing prediction engine 240 and a patient-external therapy module 250. Some or all of the implantable sensors 210 may have remote communication capabilities, such as a wireless proprietary or a wireless Bluetooth communications link. In this implementation, the wireless communications link couples the implantable sensor or sensors 210 to the patient-external disordered breathing prediction engine 240. Electrical signals representing patient conditions are produced by the implantable sensors 210 and transmitted to the patient-external disordered breathing prediction engine 240.

In another example, an implantable therapy device may incorporate a disordered breathing prediction engine 240 and one or more patient-external sensors 220. Signals representing the patient conditions may be transmitted from the patient-external sensors to the implanted prediction engine 240 over a wireless communication link.

In a further example, the prediction engine may be a patient-external device coupled wirelessly to the therapy module. Various combinations of wireless or wired connections between the patient-internal sensors 210, patient-external sensors 220, patient input devices 230, the prediction engine 240, and the therapy module 250 are possible.

The above examples provide a few of the many possible configurations that may be used to provide disordered breathing therapy based on the prediction of disordered breathing in accordance with various embodiments of the invention. It is understood that the components and functionality depicted in the figures and described herein can be implemented in hardware, software, or a combination of hardware and software. It is further understood that the components and functionality depicted as separate or discrete blocks/elements in the figures can be implemented in combination with other components and functionality, and that the depiction of such components and functionality in individual or integral form is for purposes of clarity of explanation, and not of limitation.

The methods and systems for predicting disordered breathing and providing therapy for disordered breathing as illustrated by the embodiments described herein may be used in cooperation with advanced patient management systems. Advanced patient management systems allow physicians to remotely and automatically monitor patient conditions and test physiological functions, including cardiac and respiratory functions, for example. In one example of advanced patient management, an implantable cardiac rhythm management system, such as cardiac monitor, pacemaker, defibrillator, or cardiac resynchronization device, may be equipped with various telecommunications and information technologies enabling real-time data collection, diagnosis, and treatment of the patient. Advanced patient management systems may be enhanced by real-time prediction of disordered breathing and/or long term collection of disordered breathing prediction data. Systems and methods involving advanced patient management techniques are described in U.S. Pat. Nos. 6,336,903, 6,312,378, 6,270,457, and 6,398,728 which are incorporated herein by reference in their respective entireties.

One subset of the detected patient conditions, such as the representative conditions listed in Table 1, may represent conditions that predispose the patient to disordered breathing. Predisposing conditions may be statistically associated with an onset of disordered breathing during the next few hours following the detection of the conditions leading to the disordered breathing prediction. Another subset of conditions may represent precursor conditions used to predict an imminent onset of disordered breathing that may occur within a time window measured in terms of a few minutes or seconds. Detection of patient conditions associated with disordered breathing and prediction of disordered breathing based on predisposing or precursor conditions is performed on real-time basis.

A subset of patient conditions may be used to verify or otherwise inform the disordered breathing prediction. In one example, information regarding sleep onset or sleep state, e.g., REM or non-REM sleep, may be employed in prediction of sleep disordered breathing. A subset of the conditions listed in Table 1 may be used to detect whether the patient is asleep and to track the various stages of sleep. Another subset of the conditions may be employed to detect and classify disordered breathing episodes. Table 2 below provides further examples of how some conditions listed in Table 1 may be used in disordered breathing prediction.

TABLE 2

| Condition | Examples of how condition is used in disordered breathing prediction |
|---|---|
| Heart rate | Decrease in heart rate may indicate disordered breathing episode. Decrease in heart rate may indicate the patient is asleep. |
| Heart rate variability | May be used to determine sleep state and reduction in heart rate variability is a chronic factor associated with disordered breathing. |
| Ventricular filling pressure | May be used to identify/predict pulmonary congestion associated with respiratory disturbance. |
| Blood pressure | Swings in on-line blood pressure measures are associated with apnea. |
| Snoring | Snoring is associated with a higher incidence of obstructive sleep apnea and may be used to detect disordered breathing. |
| Respiration signals/respiration patterns | Respiration patterns may be used to detect disordered breathing episodes. Respiration patterns may be used to determine the type of disordered |

TABLE 2-continued

| Condition | Examples of how condition is used in disordered breathing prediction |
|---|---|
| | breathing. |
| | Respiration patterns may be used to detect that the patient is asleep. |
| | Hyperventilation may be used to predict disordered breathing. |
| | Previous episodes of disordered breathing may be used to predict further episodes. |
| | One form of disordered breathing may be used to predict another form of disordered breathing |
| Patency of upper airway | Patency of upper airway is related to obstructive sleep apnea and may be used to detect episodes of obstructive sleep apnea. |
| Pulmonary congestion | Pulmonary congestion is associated with respiratory disturbances. |
| Sympathetic nerve activity | End of apnea associated with a spike in SNA |
| CO2 saturation | Low CO2 levels initiate central apnea. |
| O2 saturation | O2 desaturation occurs during severe apnea/hypopnea episodes. |
| Blood alcohol content | Alcohol tends to increase incidence of snoring & obstructive apnea. |
| Adrenalin | End of apnea associated with a spike in blood adrenaline. |
| Brain Natriuretic Peptide (BNP) | A marker of heart failure status, which is associated with Cheyne-Stokes Respiration |
| C-Reactive Protein | A measure of inflammation that may be related to apnea. |
| Drug/Medication/Tobacco use | These substances may affect the likelihood of both central & obstructive apnea. |
| Muscle atonia | Muscle atonia may be used to detect REM and non-REM sleep. |
| Eye movement | Eye movement may be used to detect REM and non-REM sleep. |
| Temperature | Ambient temperature may be a condition predisposing the patient to episodes of disordered breathing. |
| Humidity | Humidity may be a condition predisposing the patient to episodes of disordered breathing. |
| Pollution | Pollution may be a condition predisposing the patient to episodes of disordered breathing. |
| Posture | Posture may be used to determine if the patient is asleep and may predispose the patient to disordered breathing. Posture may be a condition predisposing the patient to episodes of disordered breathing. |
| Activity | Patient activity may be used in relation to sleep detection. |
| Sleep stage | NREM sleep may be associated with a higher probability of DB |
| Location | Patient location may used to determine if the patient is in bed as a part of sleep detection. |

Figure 3:
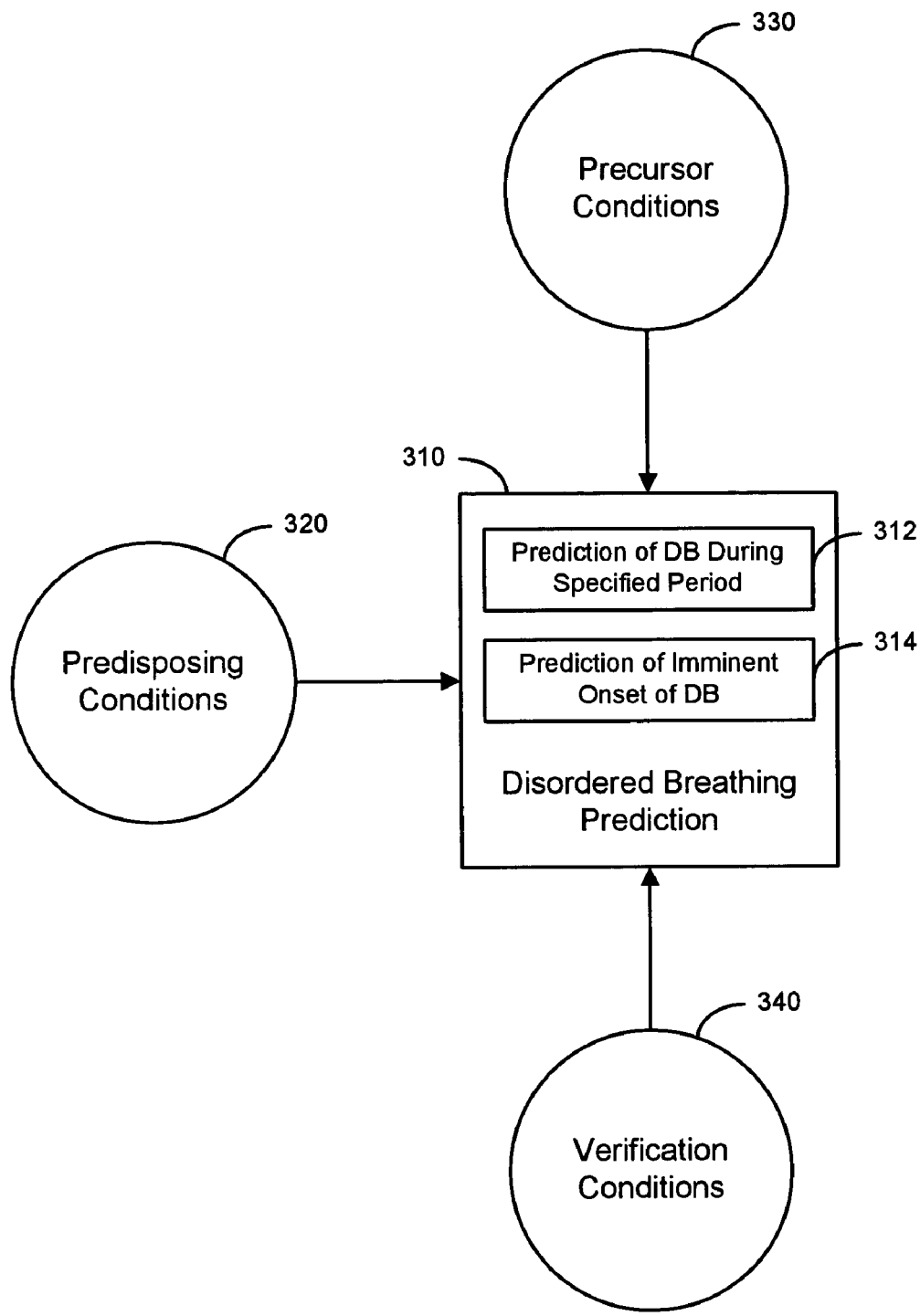
FIG. 3 illustrates conditions that may be used to predict disordered breathing according to embodiments of the invention.

FIG. 3 conceptually illustrates how patient conditions such as those listed in Table 1 and/or 2 may be used in predicting disordered breathing 310 according to embodiments of the invention. In one embodiment, the system tracks one or more of the conditions listed in Table 1, Table 2, or both, to predict disordered breathing. For example, over the course of a period of time, e.g., at least a 16 hour window preceding and including the patient's historical sleep time, the system may track one or more conditions to determine the presence and/or level of each particular condition.

In one implementation, the system tracks conditions that have been determined to predispose 320 the patient to an attack of disordered breathing. Predisposing conditions represent patient conditions statistically associated with an onset of disordered breathing. The presence of one or more predisposing conditions may indicate that disordered breathing is likely to occur within the next time period, such as an eight hour period following the disordered breathing prediction, or during the current sleep period. For example, the predisposing conditions may include the air pollution index of the patient's environment downloaded from an air quality website, recent tobacco use reported by the patient, the degree of the patient's pulmonary congestion detected by an implanted transthoracic impedance sensor, as well as other patent internally or externally detected predisposing conditions.

Additionally, or alternatively, the system may use previous episodes of disordered breathing to determine that the patient is predisposed to further episodes of disordered breathing within particular time period, such as during a sleep period. For example, previous episodes of disordered breathing during a first interval within the sleep period may be an indication that additional episodes are likely to occur in a second and subsequent interval within the same sleep period. In one example, the occurrence of a first type of disordered breathing may be used to predict a second type of disordered breathing. In another example, the periodicity of disordered breathing may be used to predict future episodes of disordered breathing.

The disordered breathing prediction engine may use the type, duration, frequency, and/or severity of the previous disordered breathing episodes to inform the disordered breathing prediction analysis. Quantification of the severity, frequency, and duration of disordered breathing may be accomplished using any of a number of disturbed breathing measures, including, for example, percent time in disordered breathing and the apnea/hypopnea index.

A further example of a condition predisposing a patient to hypopnea or apnea is body posture. A supine posture is more likely to result in obstruction of the upper airway and can be used to predict episodes of obstructive hypopnea and apnea. Posture and/or torso orientation sensing may be accomplished, for example, using an implantable multiaxis accelerometer.

As previously discussed, sleep disordered breathing is a prevalent form of disordered breathing. Thus, a patient may be more likely to experience episodes of disordered breathing when the patient is in bed sleeping. Thus, proximity to bed may be employed as a predisposing condition to disordered breathing. The disordered breathing therapy system may use a bed proximity sensor to detect that the patient is in bed. Bed proximity may be detected by placing a beacon transmitter on the patient's bed. Receiver circuitry on or in the patient, for example, incorporated in the patient's pacemaker, receives the beacon signal and determines that the patient is in bed.

Conditions that predispose the patient to disordered breathing 320 are conditions that indicate the likelihood that one or more episodes of disordered breathing will occur during the next time period, such as over the course of the night or other sleep period. Based on predisposing conditions 320, an onset of disordered breathing may be predicted 312 to occur within a time window that may include several hours, for example, eight hours.

A second set of conditions, denoted herein as precursor conditions 330, may be used to predict 314 an impending onset of disordered breathing. Precursor conditions 330 indicate that an episode of disordered breathing is imminent and will occur within a time window that may be measured in terms of minutes or seconds, for example. In one implementation, precursor conditions 330 may be used to predict that an episode of disordered breathing will occur within the next 300 seconds, for example.

In one embodiment, precursor conditions 330 indicative of an impending onset of disordered breathing may include, for example, pre-apnea or pre-hypopnea conditions. In one implementation, changes in blood gas concentration, such as $CO_2$, may be causal to central apnea. Therefore, a precursor condition of pre-apnea in a particular patient may be detected when the patient's $CO_2$ level, as measured, for example, by a patient-external $CO_2$ sensor, falls below a selected level, indicating an impending onset of an apnea episode.

In another embodiment, a patient's heart rate variability may be significantly altered before, during, and after episodes of apnea. Heart rate variability may be used, for example, as a precursor condition to predict an impending episode of disordered breathing.

In yet another embodiment, a pre-apnea or pre-hypopnea condition may be detected by analyzing the patient's respiration patterns. Respiration cycles just prior to disordered breathing event, e.g., an apnea or hypopnea event, may exhibit a characteristic pattern. For example, an apnea event for many patients is preceded by a period of hyperventilation with a number of rapid, deep breaths. The pattern of hyperventilation may be detected by analyzing patient's transthoracic impedance signal to determine respiration rate and tidal volume.

Cheyne-Stokes respiration and some apnea/hypopnea episodes may exhibit a crescendo-decrescendo respiration pattern. The crescendo-decrescendo respiration pattern produces hyperventilation during the crescendo stage and hypoventilation during the decrescendo phase. Hyperventilation, secondary to pulmonary congestion, drives arterial partial pressure of carbon dioxide down. A decrease in arterial partial pressure of carbon dioxide below an apnea level may be a causal mechanism for central apnea. According to one embodiment of the invention, detection of an impending onset of disordered breathing may be implemented by detecting a series of increasing tidal volumes followed by a series of decreasing tidal volumes.

For some patients, disordered breathing occurs at regular intervals, allowing the periodicity of the disordered breathing episodes to be used as a precursor condition. If disordered breathing episodes of the patient occur at regular intervals, the next episode of disordered breathing may be predicted based on the time elapsed since the last episode was detected.

In addition, the occurrence of one form of disordered breathing may be used to predict another form of disordered breathing. For example, a patient may characteristically experience one or more episodes of obstructive sleep apnea during the first part of the night followed by central sleep apnea episodes during the later part of the night. In another example, one or more episodes of hypopnea may be used to predict future apnea episodes.

Snoring is an additional example of a pre-apnea or pre-hypopnea condition. In many, patient snoring, or more generally any abnormal airflow in the upper airway, which may be detectable via acoustic means, precedes more significant sleep disordered breathing conditions such as hypopnea or apnea. Precursor conditions 330 may be analyzed individually, or in combination with one or more predisposing conditions 320, to predict the impending onset of a disordered breathing episode.

The conditions and associated prediction criteria used for disordered breathing prediction may be highly patient specific. Conditions that are reliably predictors of disordered breathing in one patient may not be effective for another patient. Therefore, conditions used to predict disordered breathing and the respective prediction criteria are preferably based on patient-specific data.

A subset of patient conditions may be used to verify or confirm a prediction of disordered breathing. For example, before or after a prediction of disordered breathing is made, one or more verification conditions 340 may be checked to confirm the prediction. The verification conditions, as well as the physiological and contextual conditions used to predict disordered breathing, may be highly patient specific.

In one example embodiment, a characteristic pattern of respiration is a reliable predictor of disordered breathing in a particular patient only when the patient is supine. If the prediction is made while the patient not supine, normal variations in respiration cycles in this particular patient may lead to an erroneous prediction of disordered breathing. Thus, before disordered breathing is predicted, a posture sensor signal is checked to verify that the patient is supine. If the patient is supine and the patient's respiration cycles are consistent with criteria indicating that disordered breathing is likely, the disordered breathing prediction is made.

In another example, the patient is known to suffer from episodes of apnea during sleep. The patient's sleep apnea may be predicted using a number of contextual and physiological conditions. The prediction of sleep apnea may be made after assessing that the patient's posture and location are consistent with sleep. Before a prediction of sleep apnea is made, the system confirms that the patient is lying down in bed by checking the signal from an implantable posture sensor and a bed proximity sensor.

Alternatively, or additionally, the system may detect that the patient is sleeping by examining the patient's respiration and/or activity prior to making a prediction regarding sleep disordered breathing. A method of sleep detection is described in commonly owned U.S. patent application Ser. No. 10/309,771, filed Dec. 4, 2002, which is incorporated herein by reference in its entirety.

Figure 4:
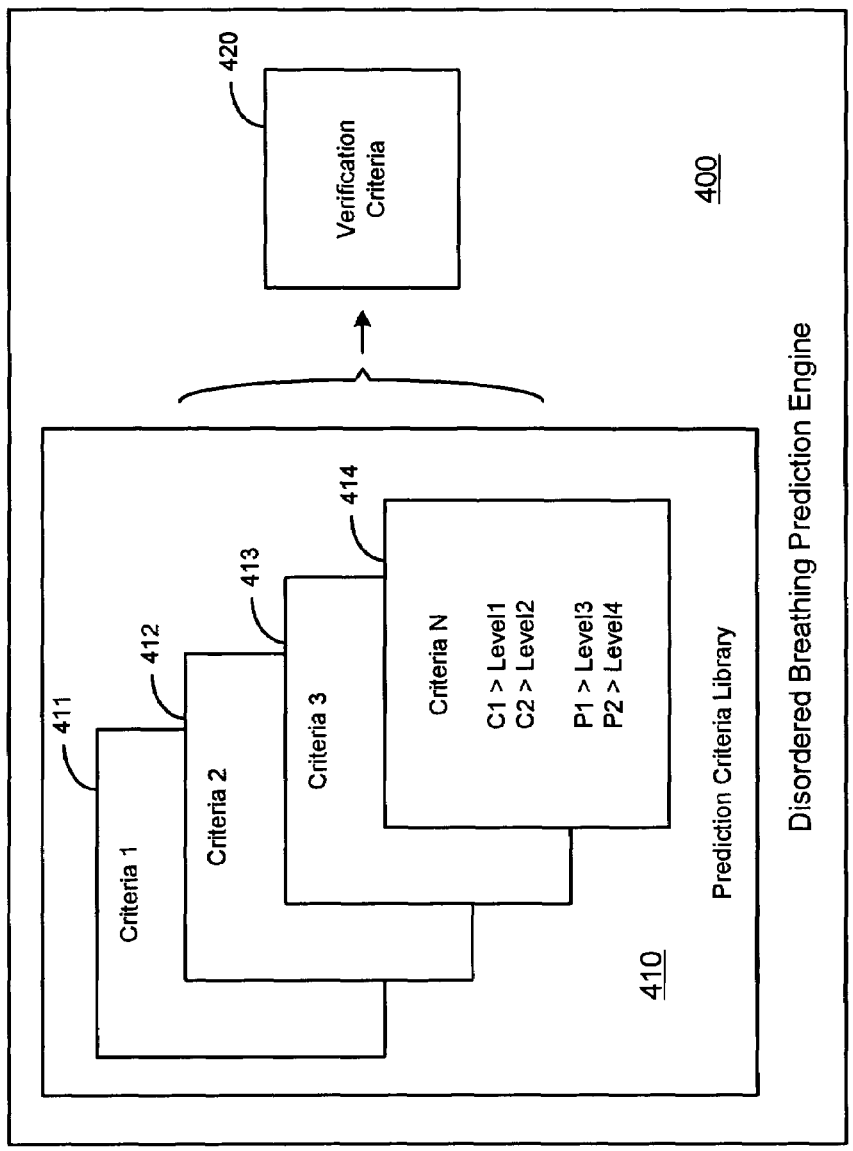
FIG. 4 is a block diagram of a disordered breathing prediction engine in accordance with embodiments of the invention.

The operation of a disordered breathing prediction engine 400, according various to embodiments, is conceptually illustrated in the block diagram of FIG. 4. Periodically, one or more patient conditions are detected and compared to a library 410 of prediction criteria. The prediction criteria library 410 may incorporate one or more sets of prediction criteria 411, 412, 413, 414. Each of these sets of criteria may be compared to the detected patient conditions. If the criteria of a prediction criteria set 411, 412, 413, 414 are substantially consistent with the patient conditions, a preliminary disordered breathing prediction may be made.

In various embodiments, the prediction criteria sets 411, 412, 413, 414 represent one or more condition thresholds associated with an onset of disordered breathing. In one example embodiment, the level of one or more detected conditions may be compared to the prediction criteria sets 411, 412 413, 414. If the levels of the one or more conditions are substantially consistent with the thresholds specified in a prediction criteria set 411, 412, 413, 414, a preliminary prediction of disordered breathing may be made.

The examples that follow are described in terms of a condition being consistent with a prediction criteria when the condition exceeds a prediction criteria threshold. However, it will be understood that different threshold requirements may be defined for different conditions. For example, one condition may be defined to be consistent with a prediction criterion when the condition exceeds a prediction criterion threshold. Another condition may be defined to be consistent with a prediction criterion threshold when the condition falls below the threshold. In yet another example, a condition may be defined to be consistent with the prediction criterion when the condition falls within a specified range of values. Patient conditions may be compared to prediction criteria based on the timing, rate of change, or maximum or minimum value of the condition, for example.

In the example provided in FIG. 4, the prediction criteria N 414 involves two contextual conditions, C1 and C2, and two physiological conditions, P1 and P2. In this particular example, if conditions C1, C2, P1, and P2 exceed levels Level1, Level2, Level3, and Level4, respectively, the patient may be likely to experience disordered breathing during the night. Therefore, when conditions C1, C2, and P1, P2 reach the levels specified in criteria N 414, preliminary prediction of disordered breathing is made.

In another embodiment of the invention, the relationships between the detected conditions are analyzed to predict disordered breathing. In this embodiment, the disordered breathing prediction may be based on the existence and relative values associated with two or more patient conditions. For example, if condition A is present at a level of x, then condition B must also be present at a level of f(x) before a disordered breathing prediction is made.

In yet another embodiment of the invention, the estimated probability, $P(C_n)$, that disordered breathing will occur if a particular condition level is detected may be expressed as a function of the ratio of the number of times disordered breathing occurred within a selected time interval following the detection of the particular condition level to the total number of observed occurrences of the condition level. The probability that disordered breathing will occur, $P(C_n)$, is compared to a threshold probability level to make the disordered breathing prediction. Other methods of calculating the estimated probability are also possible.

The prediction of disordered breathing may be based on the convergence or divergence of a number of conditions occurring within the same time period. In this situation, a composite probability score may be computed as a combination of the individual probabilities. In one embodiment, the probabilities are combined by adding the condition probabilities after multiplying each of the condition probabilities by a weighting factor. For example, if the disordered breathing prediction is based on four substantially simultaneous conditions, $C_1$, $C_2$, $C_3$, and $C_4$, the total probability score $PS_T$ may be calculated as:

$$PS_T = A \times P(C_1) + B \times P(C_2) + C \times P(C_3) + D \times P(C_4), \quad [1]$$

where A, B, C, and D are scalar weighting factors that may be used to estimate the relative importance of each of the conditions $C_1$, $C_2$, $C_3$, and $C_4$. If the probability score exceeds a selected prediction criteria threshold, then disordered breathing is predicted.

Although the above process describes combining the estimated probabilities for each condition by adding each of the estimated probabilities, other methods are also possible. For example, a detected patient condition may operate against a prediction of disordered breathing. In this situation, the estimated probability, $P_n(C_n)$, that disordered breathing will not occur if a particular condition level is detected may be expressed as a function of the ratio of the number of times disordered breathing did not occur within a selected time interval following the detection of the particular condition level to the total number of observed occurrences of the condition level. This value may be subtracted from the total to determine the probability score. Non-linear methods of combining the estimated probabilities to arrive at a composite probability are also possible.

If the conditions affecting the patient are consistent with a prediction of disordered breathing, the prediction may be verified by comparing one or more verification conditions to verification criteria. If the verification conditions are consistent with the verification criteria, a prediction of disordered breathing is made.

In the embodiments described above, predictions of disordered breathing are based upon comparisons of one or more patient conditions to sets of prediction criteria. The initial data from which the initial prediction criteria sets are formed may be derived from past observations taken from population data, or from data collected from a particular patient. The initial prediction criteria sets may then be modified as additional data are collected from the patient.

In one embodiment, an estimated accuracy for the prediction criteria is updated for every prediction event. The estimated positive predictive value (PPV) for a prediction criteria set N may be expressed as:

$$PPV_N = \frac{TP}{TP + FP} \quad [2]$$

where TP (true positive) is the number of times the prediction criteria set successfully predicted disordered breathing, and FP (false positive) is the number of times the prediction criteria erroneously predicted disordered breathing.

If the estimated accuracy of prediction criteria set N, $PPV_N$, falls below a predetermined level, for example, 0.7, the prediction criteria set N may be modified. In one embodiment, a possible prediction criteria set is formed, for example, by modifying the threshold level of one or more of the conditions represented by the original prediction criteria set N. In one embodiment, each threshold in the original prediction criteria set N is modified by an incremental value, to make the prediction criteria set more accurate.

In another embodiment, conditions represented in the original prediction criteria set N are compared to the conditions that are present just prior to a disordered breathing occurrence to determine how the modification for the possible prediction criteria set should be implemented. For example, if the level of a particular condition just prior to the occurrence shows a relatively large variation just prior to the disordered breathing episode, but the levels of other conditions remain constant, then only the changing level may be modified in the possible prediction criteria set.

Each time the possible prediction criteria set is satisfied, no prediction of disordered breathing is made, however, the accuracy of the possible prediction criteria set is updated, for example, using an equation similar in form to Equation 2. If the accuracy of the possible prediction criteria set reaches a selected level, for example, 0.7, and the accuracy original prediction criteria set N remains below 0.7, the possible prediction criteria set may replace the original prediction criteria set N in the prediction criteria library.

According to various embodiments, new prediction criteria sets may be added to the prediction criteria library. In accordance with these embodiments, if a disordered breathing episode occurs without prediction, the levels of the detected patient conditions prior to the disordered breathing episode are saved as a possible prediction criteria set. Each time the possible prediction criteria set is satisfied, no prediction of disordered breathing is made, however, the accuracy of the possible prediction criteria set is updated, for example, using an equation similar in form to Equation 2. If the accuracy of the possible prediction criteria set reaches a selected level, for example, 0.7, the possible prediction criteria set may be added to the prediction criteria library.

The system may also be adjusted to provide increasingly sensitive disordered breathing prediction criteria sets, according to various embodiments. The estimated sensitivity for a prediction criteria set N may be expressed as:

$$Sensitivity_N = \frac{TP}{TP + FN} \quad [3]$$

where TP (true positive) is the number of times the prediction criteria successfully predicted disordered breathing, and FN (false negative) is the number of times the prediction criteria erroneously predicted that disordered breathing would not occur.

In one embodiment, if the prediction criteria accuracy for the prediction criteria set N becomes larger than a selected number, for example, 0.9, then the threshold levels of one or more of the conditions represented in the prediction criteria set N may be adjusted to provide enhanced sensitivity.

In one example, the threshold level of each condition represented in the prediction criteria set N is modified by an incremental value, thus making the prediction criteria set N more sensitive. In another embodiment, conditions represented in the prediction criteria set N are compared to the conditions that are present just prior to a disordered breathing occurrence to determine how the modification of the prediction criteria set N should be implemented. In yet another embodiment, a condition threshold level that is modified is based upon the relative importance of the condition in the overall prediction criteria. In another example, if the level of a particular condition is changing just prior to the occurrence of the disordered breathing episode, but the levels of other conditions remain constant, only the changing condition may be modified.

Following adjustment by any of the processes described above, the adjusted prediction criteria set may be designated as a possible prediction criteria set. Each time the possible prediction criteria set is satisfied, no prediction of disordered breathing is made, however, the accuracy of the possible prediction criteria set is updated, for example, using Equation 2 or 3. If the accuracy of a possible prediction criteria set reaches a selected level, for example, 0.7, the possible prediction criteria set may be added to the prediction criteria library.

The system may also be adjusted to provide improved specificity or a negative predictive value (NPV) of disordered breathing prediction criteria in a manner similar to the adaptive method described previously. Calculation of specificity and NPV for a prediction criteria N may be accomplished using equations 4 and 5 below.

$$Specificity_N = \frac{TN}{TN + FP} \quad [4]$$

$$NPV_N = \frac{TN}{TN + FN} \quad [5]$$

where TN (true negative) is the number of times the prediction criteria successfully predicted the absence of disordered breathing, FP (false positive) is the number of times the prediction criteria erroneously predicted disordered breathing and FN (false negative) is the number of times the prediction criteria erroneously predicted the absence of disordered breathing.

Figure 5:
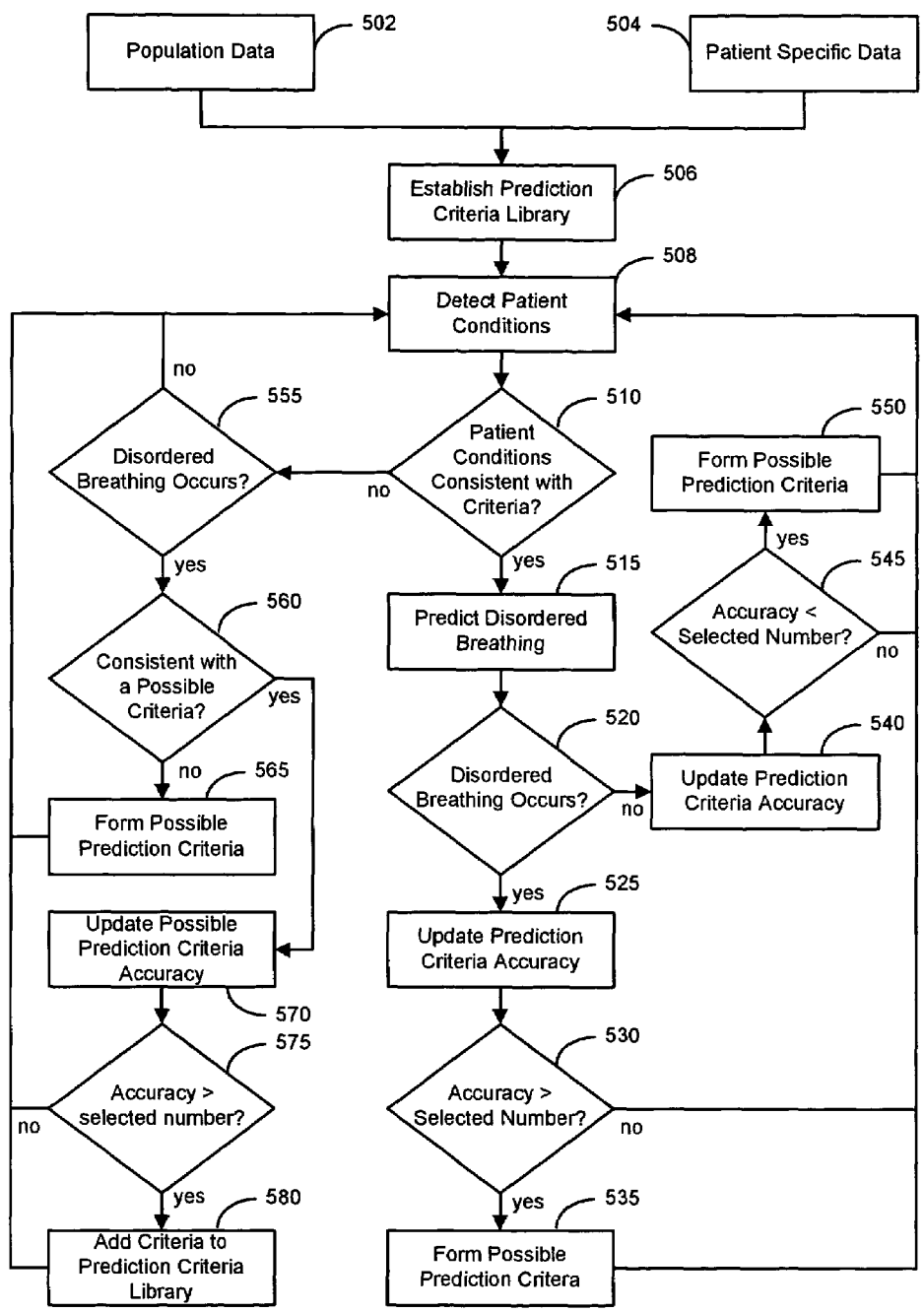
FIG. 5 is a flow graph illustrating a method of updating a prediction criteria library according to embodiments of the invention.

The flowchart of FIG. 5 illustrates a method for establishing and updating the prediction criteria library according to embodiments of the invention. Previous observations of disordered breathing may be assimilated from population data 502 or from past observation of the specific patient 504. One or more prediction criteria sets are determined and organized in a prediction criteria library 506.

Conditions associated with disordered breathing are periodically detected 508 and compared to the prediction criteria sets in the prediction criteria library. If the conditions are consistent 510 with any of the prediction criteria sets in the library, then disordered breathing is predicted 515. Within a selected time window following the disordered breathing prediction, the system determines if disordered breathing occurs 520.

One illustrative approach to detecting disordered breathing involves monitoring a respiratory waveform output, for example, using a transthoracic impedance sensor. When the tidal volume (TV) of the patient's respiration, as indicated by the transthoracic impedance signal, falls below a hypopnea threshold, then a hypopnea event is declared. For example, a hypopnea event may be declared if the patient's tidal volume fall below about 50% of the recent average tidal volume or other baseline tidal volume. When the patient's tidal volume falls further to an apnea threshold, e.g., about 10% of the recent average tidal volume, an apnea event is declared.

Other approaches to detecting disordered breathing are described in commonly owned U.S. patent application Ser. No. 10/309,770, filed Dec. 4, 2002, which is incorporated herein by reference in its entirety.

If disordered breathing occurs 520, the prediction criteria accuracy of the prediction criteria set used for the disordered breathing prediction is updated 525. If the updated prediction criteria accuracy is greater 530 than a selected number, then a possible prediction criteria set is formed 535. The possible prediction criteria set may be formed, for example, by substituting more sensitive condition levels when compared to the original prediction criteria set.

If disordered breathing is not detected 520 following the prediction, then the prediction criteria set accuracy is updated 540. If the prediction criteria set accuracy decreases 545 below a selected number, then a possible prediction criteria set 550 is formed. The possible prediction criteria set may be formed, for example, by substituting more stringent condition levels to produce a more accurate prediction.

If the detected patient conditions are not consistent 510 with any of the prediction criteria sets in the prediction criteria library, disordered breathing is not predicted. Within a time window following the disordered breathing prediction, the system determines if disordered breathing occurs 555. If disordered breathing occurs 555, then the system checks to see if the patient conditions are consistent 560 with any of the possible prediction criteria sets. If the patient conditions are not consistent 560 with any of the possible prediction criteria sets, a possible prediction criteria set is formed 565.

If the patient conditions are consistent 560 with a possible criteria set, the possible prediction criteria set accuracy is updated 570. If the possible prediction criteria accuracy increases beyond a selected number 575, the possible prediction criteria set is added 580 to the prediction criteria library.

Figure 6:
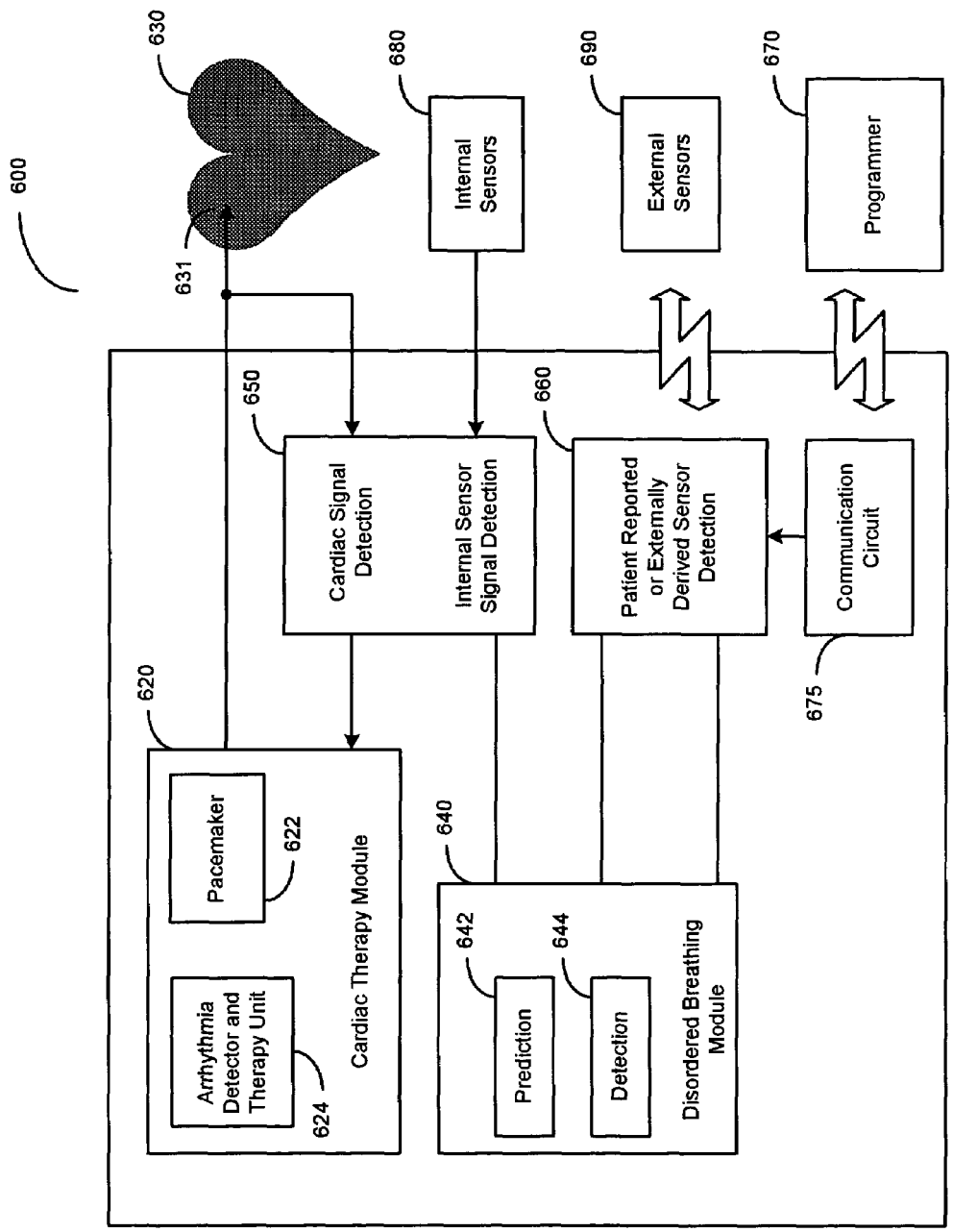
FIG. 6 is a block diagram of a cardiac rhythm management system incorporating a disordered breathing prediction engine in accordance with embodiments of the invention.

The block diagram of FIG. 6 illustrates a disordered breathing therapy system configured in accordance with embodiments of the invention. According to one embodiment, a disordered breathing prediction engine 642 is incorporated within a cardiac rhythm management system 600. The cardiac rhythm management system may include, for example, a cardiac therapy module 620 including a pacemaker 622 and an arrhythmia detector/therapy unit 624. The cardiac therapy module 620 is coupled to a lead system having electrodes 631 implanted to electrically couple the heart 630 to the cardiac rhythm management system 600.

The cardiac rhythm management system 600 includes circuitry 650 for detecting signals from patient-internal sensors such as the implanted cardiac electrodes 631, and other patient-internal sensors 680, such as the patient-internal sensors listed in Table 1. The patient-internal sensors 680 may be coupled to the implanted signal detection circuitry 650 through conducting leads as shown, or through a wireless connection, for example.

The cardiac rhythm management system 600 may also include circuitry 660 for detecting signals from patient-external sensors 690 located outside the patient's body and from patient-reported input. The patient-external sensors 690 may be coupled to the detection circuitry 660 through a wireless link. Signals representing patient-reported data may be input through a programmer unit 670 that is wirelessly coupled to a telemetry circuit 675 within the cardiac rhythm management system 600.

The cardiac therapy module 620 receives cardiac signals from the implanted cardiac electrodes 631 and analyzes the cardiac signals to determine an appropriate therapy. The cardiac therapy may include pacing therapy controlled by the pacemaker 622 to treat cardiac rhythms that are too slow. The pacemaker 622 controls the delivery of periodic low energy pacing pulses to one or more of the heart chambers through cardiac electrodes 631 to ensure that the periodic contractions of the heart are maintained at a hemodynamically sufficient rate.

The cardiac therapy may also include therapy to terminate tachyarrhythmia, wherein the heart rate is too fast. The arrhythmia detector/therapy unit 624 detects and treats episodes of tachyarrhythmia, including tachycardia and/or fibrillation. The arrhythmia detector/therapy unit 624 recognizes cardiac signals indicative of tachyarrhythmia and delivers high energy stimulations to the heart 630 through the implanted electrodes 631 to terminate the arrhythmia.

A disordered breathing module 640 incorporated within the cardiac rhythm management system 600 includes circuitry for disordered breathing detection 644, as well as the disordered breathing prediction engine 642. The implanted signal detection circuitry 650 and patient-reported/patient-external sensor detection circuitry 660 are coupled to the disordered breathing module 640. The implanted signal detection circuitry 650 and patient-reported/patient-external sensor detection circuitry 660 provide signals associated with various patient conditions used for disordered breathing detection and prediction.

A prediction of disordered breathing by the disordered breathing prediction engine 642 may be used to trigger cardiac pacing therapy delivered by the cardiac therapy module 620 to mitigate disordered breathing. In one example, the cardiac therapy module 620 delivers an appropriate electrical stimulation therapy to the patient's heart 630 through electrodes 631 coupled to the patient's heart. In one example therapy regime, electrical stimulation therapy to mitigate disordered breathing may include pacing at a rate exceeding an intrinsic rate or in excess of the patient's normal sleep rate. The pacing may involve any or all of the heart chambers, for example, right and left atria and right and left ventricles. The pacing may also involve bi-atrial, bi-ventricular, or multi-site pacing. In one example, the pacing pulses may be delivered to left and right atria simultaneously, or according to other timing sequences. In another example, the simultaneous or otherwise timed pacing pulses may be delivered to the left and right ventricles of the heart.

Further, adapting a cardiac electrical therapy to mitigate disordered breathing may involve adapting a therapy involving non-excitatory electrical stimulation of one or more heart chambers, e.g., the left and/or right ventricles, or other cardiac sites. Non-excitatory electrical stimulation may be delivered during absolute refractory periods of the cardiac tissue, for example, to improve cardiac contractility. The non-excitatory stimulation therapy may be used alone or in combination with cardiac pacing to provide a comprehensive therapy regimen for patients with CHF and disordered breathing such as Cheyne-Stokes respiration.

Figure 7:
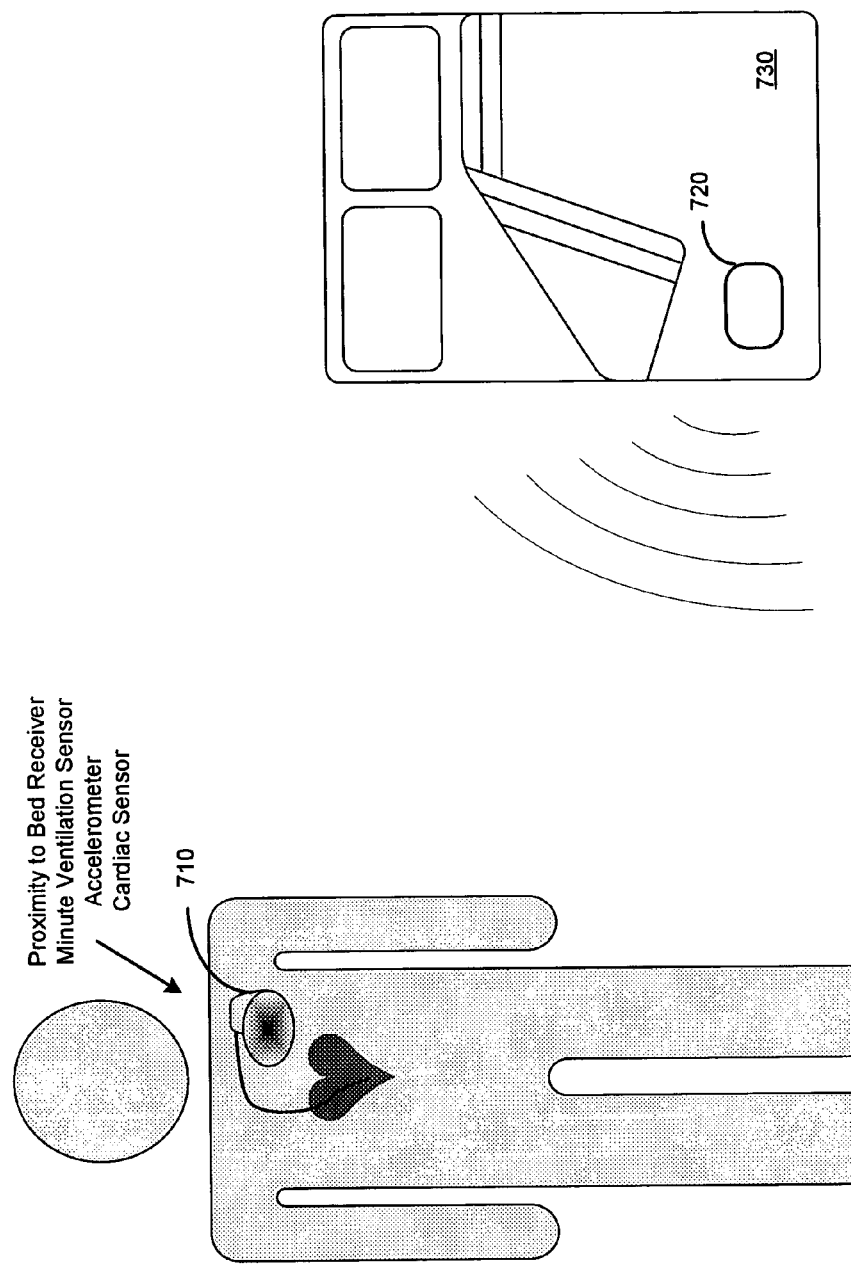
FIG. 7 is a diagram illustrating a system for predicting disordered breathing in accordance with embodiments of the invention.
Figure 8A:
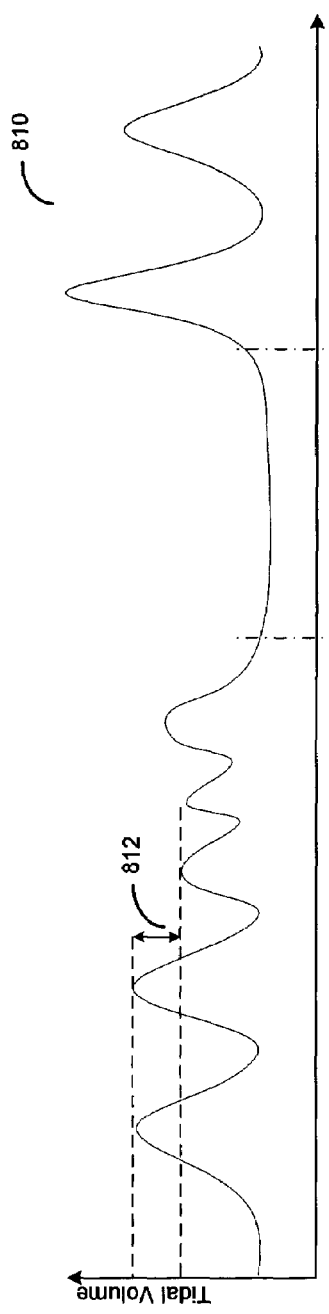
FIG. 8A illustrates a representative graph of tidal volume signal used in connection with disordered breathing prediction in accordance with embodiments of the invention.
Figure 8B:
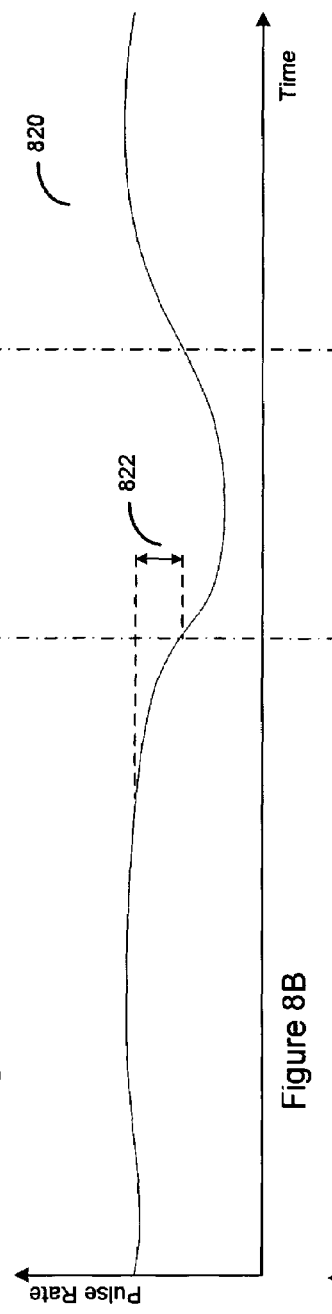
FIG. 8B illustrates a representative graph of heart rate signal used in connection with disordered breathing prediction in accordance with embodiments of the invention.
Figure 8C:
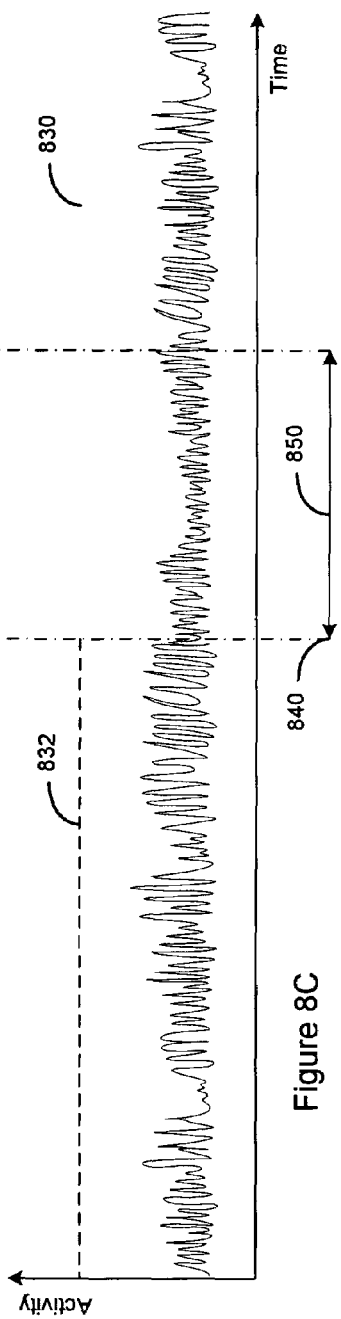
FIG. 8C illustrates a representative graph of an activity signal used in connection disordered breathing prediction in accordance with embodiments of the invention.
Figure 9:
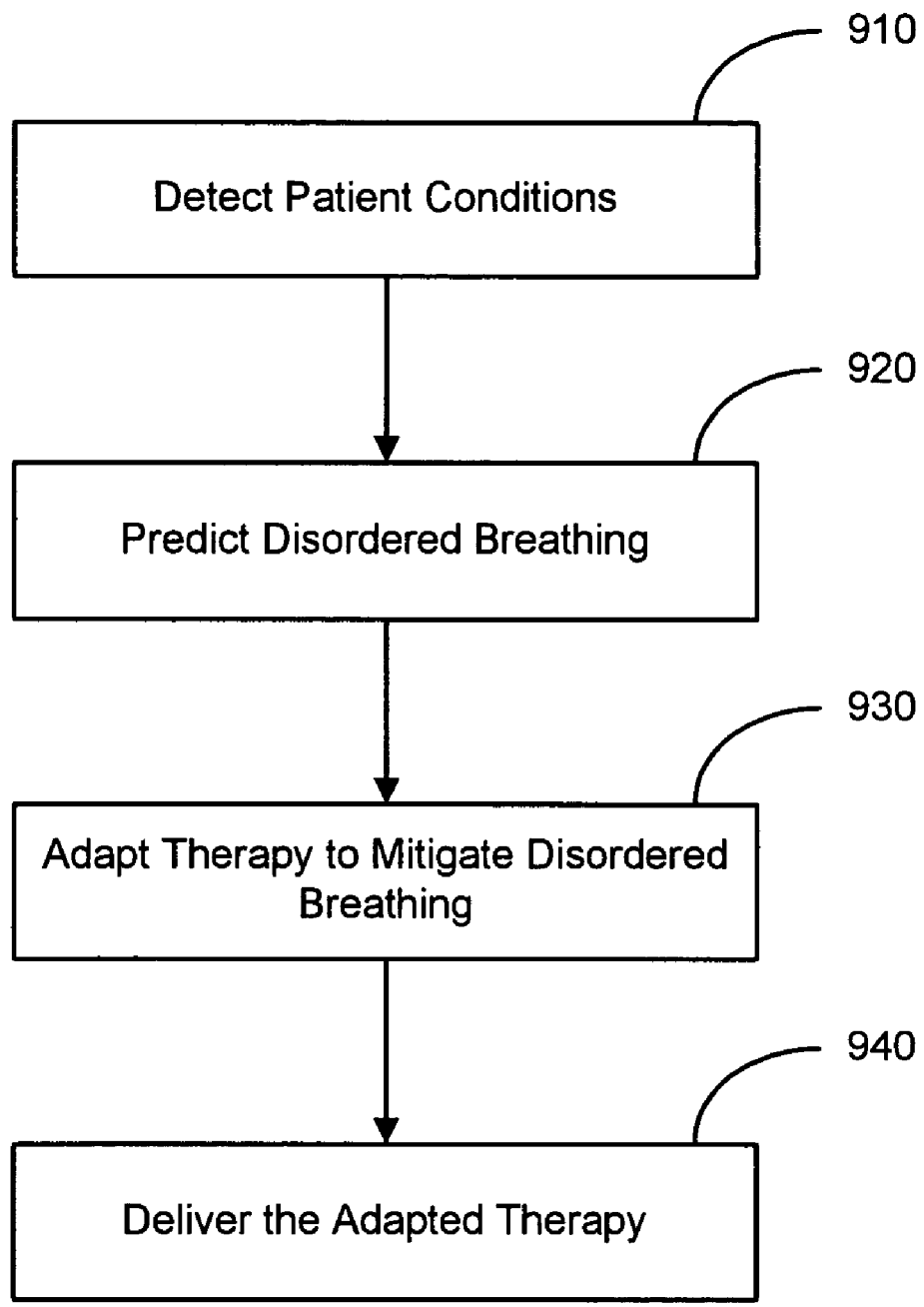
FIG. 9 is a flow graph of a method for delivering an adapted therapy for disordered breathing in accordance with embodiments of the invention.

FIGS. 7 through 9 illustrate systems that may be used to implement methods of disordered breathing prediction according to embodiments of the invention. FIG. 7 illustrates a system for delivering disordered breathing therapy utilizing the cardiac rhythm management system incorporating a disordered breathing prediction engine 710 as discussed in connection with FIG. 6. In addition to the previously described implanted cardiac electrodes, the cardiac rhythm management system 710 also includes an accelerometer mounted within the housing of the cardiac rhythm management system 710 for sensing patient activity.

In the embodiment of FIG. 7, the cardiac rhythm management system 710 further includes a receiver for a proximity to bed signal that is generated by a proximity to bed beacon 720 located on or near the patient's bed 730. If the proximity to bed receiver detects a signal of sufficient strength from the proximity to bed beacon 720, then the receiver signals that the patient is in bed.

The cardiac rhythm management system 710 includes a transthoracic impedance sensor used to determine patient conditions including respiration rate, respiration rate variability, tidal volume, and minute ventilation, for example. In this example, the disordered breathing prediction engine located within the cardiac rhythm management system 710 predicts disordered breathing based primarily on the patient's heart rate and tidal volume. Two additional signals, the patient's activity level and proximity to bed, are used to verify the prediction of disordered breathing. After a prediction of disordered breathing, the cardiac rhythm management system delivers an appropriate cardiac therapy to mitigate the disordered breathing.

Representative graphs of the patient's tidal volume 810, heart rate 820, and activity level 830 during disordered breathing prediction are illustrated in FIGS. 8A-8C. In this example, the patient's tidal volume 810 exhibits a characteristic decrease 812 just before the onset 840 of an episode of disordered breathing 850. Accordingly, a first condition threshold for disordered breathing prediction is established as a percentage drop in tidal volume. Additionally, the patient's heart rate 820 exhibits a decrease 822 that occurs substantially simultaneously with the decrease in tidal volume 812. A second condition threshold for disordered breathing detection is established as a percentage drop in heart rate. If disordered breathing is predicted, therapy may be delivered to the patient, for example, in accordance with various cardiac pacing regimens described above.

Therapy delivered to mitigate disordered breathing may be adjusted based on an assessment of the therapy. Therapy assessment may include, for example, assessment of the efficacy of therapy or assessment of the impact of the therapy on the patient. According to various embodiments, therapy efficacy may be analyzed and the therapy regimen may be adapted to provide more effective therapy. For example, if a delivered therapy does not prevent or otherwise mitigate the patient's disordered breathing, the therapy may be modified to include a more aggressive therapy regimen, e.g., cardiac pacing at a higher rate.

According to embodiments of the invention, the therapy may be adapted to reduce the impact of the therapy on the patient, e.g., to minimally impact the patient. In adapting a reduced impact therapy, the system may take into account various conditions for evaluating the impact of the therapy on the patient. For example, conditions such as patient comfort, as indicated by patient feedback, stress on physiological systems involved in the disordered breathing therapy, interaction with cardiac pacing algorithms, e.g., bradycardia pacing, cardiac resynchronization pacing an/or anti-tachycardia pacing, as determined by interactive effects of the disordered breathing therapy with cardiac pacing, and/or sleep quality, as measured by one or more sleep quality indices, may be taken into account to adapt a therapy that reduces an impact of the therapy on the patient.

In addition, impact to the patient may involve reduction of the useful service life of an implantable therapeutic device used to deliver disordered breathing therapy and/or pacing therapy for cardiac dysfunction. For example, a level of disordered breathing therapy may be unacceptably high if the energy requirements of the therapy result in an excessively reduced device service life. In this situation, early device removal and replacement produces a negative impact to the patient. Therefore, cardiac electrical therapy to mitigate disordered breathing may be adapted based on a projected reduction in device service life.

In one example implementation, pacing above a normal sleep rate may mitigate disordered breathing, but may coincidentally interrupt the patient's sleep, causing sleep fragmentation and other undesirable effects. The therapy may be adapted to reduce an impact of the therapy on the patient. For example, if the delivered therapy causes an undesirable number of arousals from sleep, the therapy may be adjusted to a less aggressive therapy regimen, e.g., cardiac pacing at a lower rate.

In another example, the therapy delivered to mitigate disordered breathing may be adapted to reduce interactions between the disordered breathing therapy and other therapies delivered to the patient. For example, some patients may receive one cardiac electrical stimulation therapy to treat disordered breathing and other cardiac stimulation therapy to treat cardiac disorders such as bradycardia or CHF. Interactions may occur between cardiac electrical therapy to mitigate disordered breathing and the patient's cardiac pacing regimen, e.g., pacing for bradycardia or cardiac resynchronization. Such interactions may be factored into the assessment of the impact disordered breathing therapy on the overall therapy delivered to the patient.

In some cases cardiac electrical therapy to mitigate disordered breathing may enhance cardiac pacing therapy directed to alleviate a cardiac dysfunction, e.g., bradycardia or CHF. For example, non-excitatory electrical stimulation of the left ventricle during an absolute refractory period may be beneficial to treat CHF and disordered breathing. In other cases, cardiac electrical therapy for disordered breathing may work at cross purposes with the patient's cardiac pacing regimen. For example, pacing therapy delivered to treat disordered breathing may increase the percentage of heart beats initiated by atrial pacing while cardiac resynchronization therapy may be optimal when intrinsic atrial events are allowed to initiate a heart beat. Evaluating the impact of disordered breathing therapy on the patient preferably takes into consideration the impact of disordered breathing therapy on the overall therapeutic goals for the patient, including cardiac pacing goals and disordered breathing goals.

FIG. 9 is a flowchart illustrating a method of providing therapy for disordered breathing according to embodiments of the invention. According to this method, one or more patient conditions are detected 910 and a first group of the detected conditions are used to predict 920 disordered breathing. A therapy is adapted to mitigate 930 or prevent the disordered breathing based on a second set of the patient conditions. The adapted therapy is delivered 940 to the patient.

A representative set of the first and second groups of patient conditions that may be used for disordered breathing prediction and therapy assessment, respectively, is provided in Table 1. As previously discussed, a first group or subset of conditions is used in connection with disordered breathing prediction. a second group of conditions, possibly overlapping the first group, is used for therapy assessment. Several aspects of therapy may be assessed. In one embodiment, therapy is assessed based on therapy effectiveness. In another embodiment, therapy is assessed based on minimal impact to the patient. In yet a further embodiment, therapy is assessed based on a combination of therapy effectiveness and minimal impact to the patient.

As previously discussed, therapy assessment may be implemented by detecting and analyzing one or more patient conditions. Conditions used to assess therapy effectiveness may be different from, or the same as, conditions used to assess the impact of the therapy on the patient. Table 3 provides a representative set of conditions that may be used for therapy assessment.

TABLE 3

| Condition | Therapy Impact | Therapy Efficacy |
|---|---|---|
| Arousal-Based Sleep Fragmentation Measures | May be used to assess therapy impact during sleep. | |
| Restful sleep (Patient reported) | May be used to assess therapy impact during sleep. | |
| Discomfort (Patient reported) | May be used to assess therapy | |

TABLE 3-continued

| Condition | Therapy Impact | Therapy Efficacy |
|---|---|---|
| Pacing algorithm interaction | impact.<br>May be used to assess therapy impact. | |
| Remaining useful life of therapy device | May be used to assess therapy impact. | |
| Pacing algorithm interaction | May be used to assess therapy impact during sleep. | |
| Disturbed Breathing-Based Measures | | May be used to analyze/assess efficacy of therapy to mitigate disordered breathing episodes. |
| Respiration quality (Patient reported) | | May be used to analyze/assess efficacy of therapy to mitigate disordered breathing episodes. |
| Heart rate variability (HRV) | | Disordered breathing causes heart rate variability to decrease. Therapy may be modified based on changes in HRV |
| Blood pressure | | Disordered breathing causes blood pressure increase |
| Sympathetic nerve activity (SNA) | | Changes in sympathetic nerve activity are caused by disordered breathing. Therapy may be adjusted based on the level of SNA |
| Blood chemistry | | A number of disordered breathing related changes may occur in a patient's blood chemistry, including, e.g., higher norepinephrine levels, and lower $PaCO_2$ |

It is understood that the patient conditions that may be used in connection with prediction of disordered breathing and/or therapy assessment are not limited to the representative sets listed in Tables 1-3. Further, although illustrative sensing methods for detecting the patient conditions are provided, it is understood that the patient conditions may be sensed and detected using a wide variety of technologies. The embodiments and features described in the instant disclosure are not limited to the particular patient conditions or the particular sensing technologies described herein.

In one example, conditions related to sleep quality, e.g., sleep fragmentation and other arousal-based measures, patient-reported restful sleep, and discomfort during therapy, may be used to assess the impact of the therapy on the patient. For example, if a patient receiving effective disordered breathing therapy has low sleep fragmentation, reports restful sleep, and reports no discomfort, the adverse effects of the therapy on the patient may be relatively low. If sleep fragmentation is relatively high, or if the patient reports discomfort or feeling tired after sleeping, these conditions may indicate that therapy is causing sleep disturbance and/or other undesirable effects. Various methods and systems for collecting sleep quality data and assessing sleep quality are described in a commonly owned U.S. patent application Ser. No. 10/642,998 filed Aug. 18, 2003 entitled "Sleep Quality Data Collection and Evaluation,", now U.S. Publication No. 2005/0042589, filed concurrently with this application which is hereby incorporated herein by reference.

Sleep fragmentation and sleep disruptions may also occur if disordered breathing therapy is ineffective and disordered breathing occurs during sleep. Therefore, a therapy impact assessment based on detected sleep quality and/or patient-reported restful sleep preferably takes into account an assessment of therapy effectiveness.

Some patients may receive cardiac electrical stimulation therapy for both disordered breathing as well as cardiac disorders such as bradycardia and/or CHF. Interactions may occur between cardiac electrical therapy to mitigate disordered breathing and the patient's cardiac pacing regimen, e.g., pacing for bradycardia or cardiac resynchronization. Such interactions may be factored into the assessment of the impact of disordered breathing therapy on the overall therapy delivered to the patient.

Interactions between cardiac therapy and disordered breathing therapy may occur, and detection of the interactions may be used to adjust therapy. In some cases, cardiac electrical therapy to mitigate disordered breathing may enhance cardiac pacing therapy directed to alleviate a cardiac dysfunction, such as bradycardia or CHF. For example, non-excitatory electrical stimulation of the left ventricle during an absolute refractory period may be beneficial to treat both CHF and disordered breathing.

In other examples, cardiac electrical therapy for disordered breathing may work at cross purposes with the patient's cardiac pacing regimen. A pacing therapy delivered for treatment of disordered breathing may increase the percentage of heart beats initiated by atrial pacing. However, a concurrent cardiac resynchronization therapy may be optimal when intrinsic atrial events are allowed to initiate a heart beat. In this situation, the disordered breathing therapy, the cardiac resynchronization therapy, or both therapies, may be adjusted to reduce undesirable therapy interactions.

The effectiveness of disordered breathing therapy may be assessed by detecting and analyzing episodes of disordered breathing that occur even though therapy is being delivered to mitigate disordered breathing. As indicated, a number of conditions listed in Table 3 may be used in connection with the detection of disordered breathing. Methods and systems for detecting and assessing disordered breathing using one or more detected patient conditions is described in commonly owned U.S. patent application Ser. No. 10/309,770, filed Dec. 4, 2002, entitled "Detection of Disordered Breathing."

Figure 10:
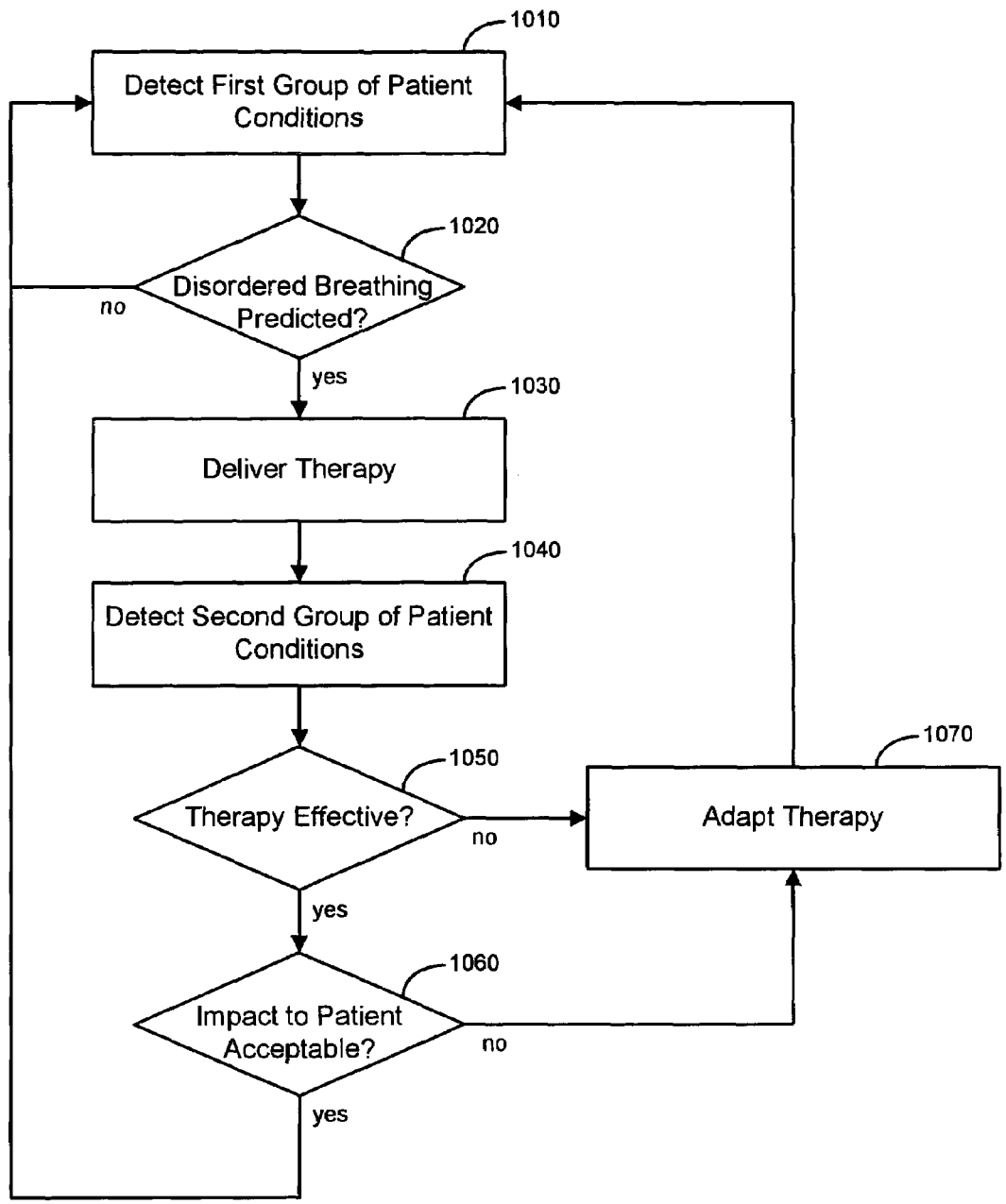
FIG. 10 illustrates adjustment of an activity sleep threshold using an MV condition in accordance with embodiments of the invention.

The flowchart of FIG. 10 illustrates a method of providing disordered breathing therapy in accordance with embodiments of the invention. A first group of patient conditions is detected 1010 and disordered breathing predicted 1020 based on the first group of patient conditions. Therapy to mitigate or prevent the disordered breathing is delivered 1030. A second group of conditions is detected 1040 and used to assess 1050 the effectiveness of the therapy. The second group of conditions may include, for example, conditions used to detect disordered breathing and analyze the type, frequency, duration, and severity of disordered breathing episodes. If therapy is ineffective 1060, the therapy regimen may be adjusted 1070.

One or more conditions of the second group of conditions are used to assess 1060 the impact of the therapy on the patient. If the therapy impacts the patient negatively, for example, by disrupting sleep or causing discomfort, then therapy parameters may be adjusted, e.g., to provide a less aggressive therapy regimen.

Figure 11:
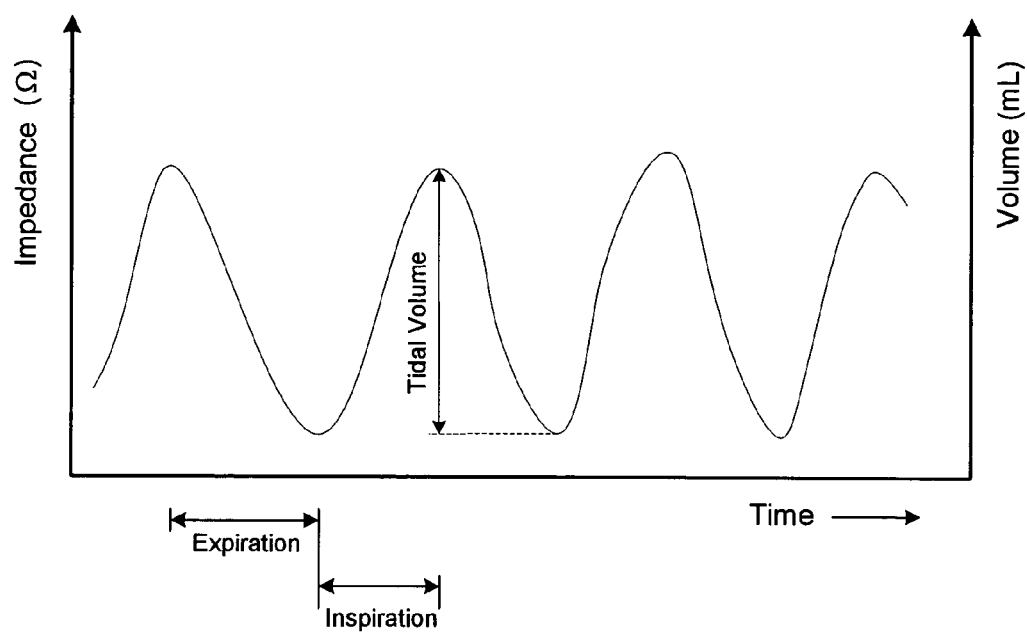
FIG. 11 illustrates a normal respiration pattern as represented by a transthoracic impedance sensor signal.

According to various embodiments of the invention, disordered breathing detection may be used to assess therapy effectiveness. In one example implementation, episodes of disordered breathing are detected by analyzing the patient's respiration. FIG. 11 illustrates a normal respiration pattern as represented by a transthoracic impedance sensor signal. The transthoracic impedance increases during respiratory inspiration and decreases during respiratory expiration. During Non-REM sleep, a normal respiration pattern includes regular, rhythmic inspiration-expiration cycles without substantial interruptions.

In one embodiment, episodes of disordered breathing may be detected by monitoring the respiratory waveform output of the transthoracic impedance sensor. When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of the recent average tidal volume or other baseline tidal volume. When the patient's tidal volume falls further to an apnea threshold, e.g., about 10% of the recent average tidal volume, an apnea event is declared.

Figure 12:
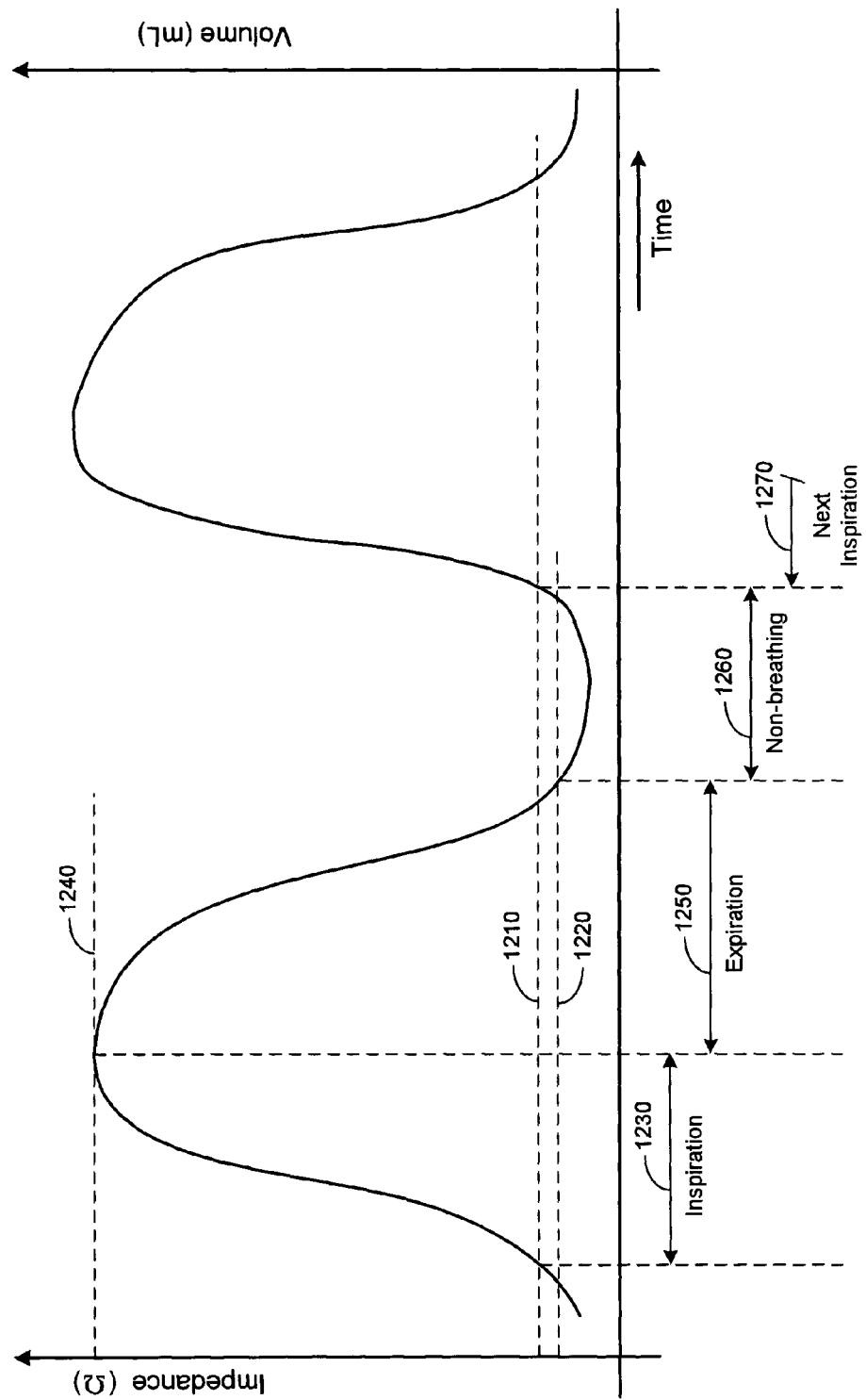
FIG. 12 illustrates respiration intervals used for disordered breathing detection according to embodiments of the invention.

In another embodiment, detection of disordered breathing, including, for example, sleep apnea and hypopnea, involves defining and examining a number of respiratory cycle intervals. FIG. 12 illustrates respiration intervals used for disordered breathing detection according to an embodiment of the invention. A respiration cycle is divided into an inspiration period corresponding to the patient inhaling, an expiration period, corresponding to the patient exhaling, and a non-breathing period occurring between inhaling and exhaling. Respiration intervals are established using inspiration 1210 and expiration 1220 thresholds. The inspiration threshold 1210 marks the beginning of an inspiration period 1230 and is determined by the transthoracic impedance signal rising above the inspiration threshold 1210. The inspiration period 1230 ends when the transthoracic impedance signal is maximum 1240. A maximum transthoracic impedance signal 1240 corresponds to both the end of the inspiration interval 1230 and the beginning of the expiration interval 1250. The expiration interval 1250 continues until the transthoracic impedance falls below an expiration threshold 1220. A non-breathing interval 1260 starts from the end of the expiration period 1250 and continues until the beginning of the next inspiration period 1270.

Figure 13:
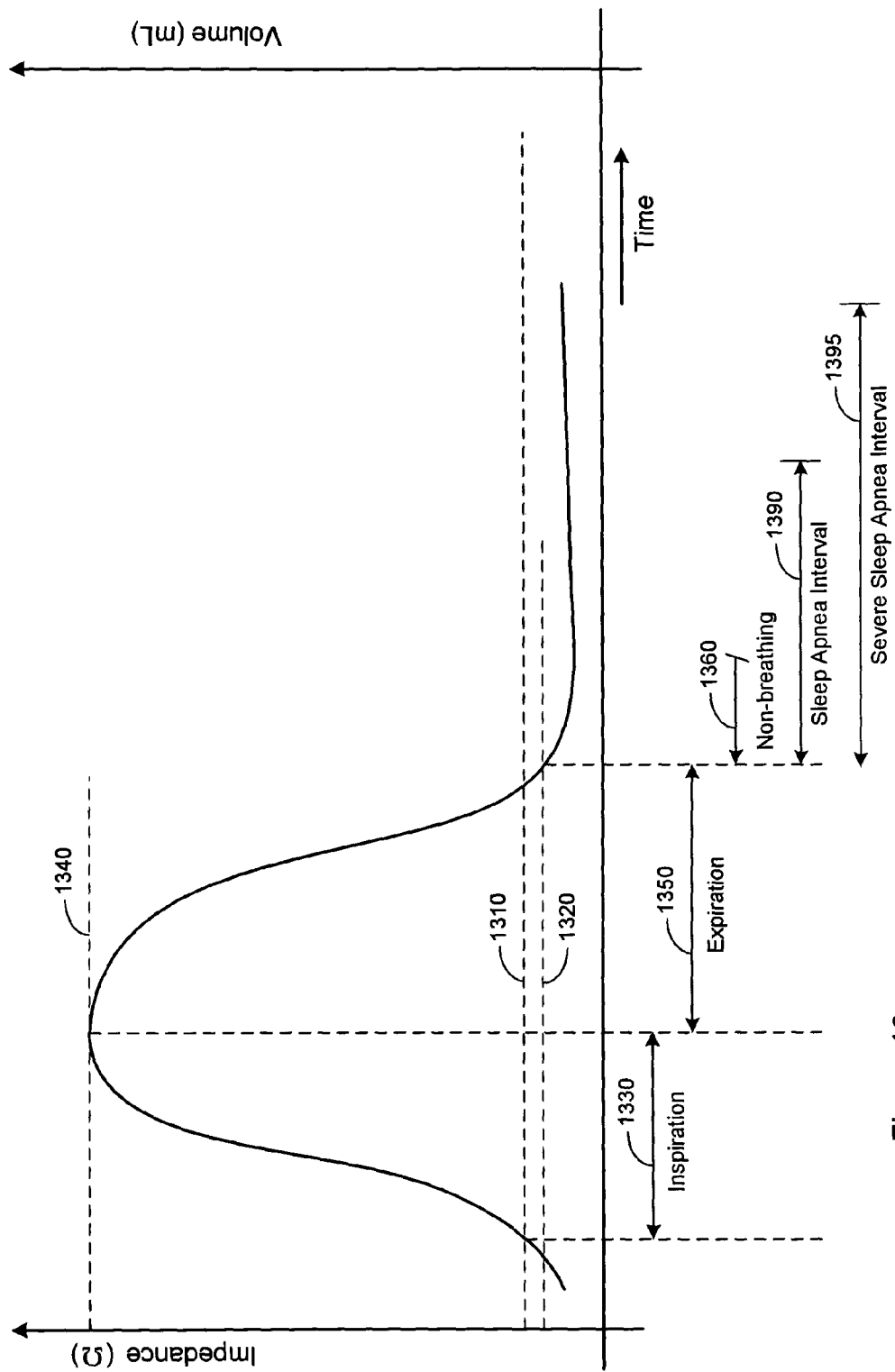
FIG. 13 illustrates detection of sleep apnea and severe sleep apnea according to embodiments of the invention.

Detection of sleep apnea and severe sleep apnea according to embodiments of the invention is illustrated in FIG. 13. The patient's respiration signals are monitored and the respiration cycles are defined according to inspiration 1330, expiration 1350, and non-breathing 1360 intervals as described in connection with FIG. 12. A condition of sleep apnea is detected when a non-breathing period 1360 exceeds a first predetermined interval 1390, denoted the sleep apnea interval. A condition of severe sleep apnea is detected when the non-breathing period 1360 exceeds a second predetermined interval 1395, denoted the severe sleep apnea interval. For example, sleep apnea may be detected when the non-breathing interval exceeds about 10 seconds, and severe sleep apnea may be detected when the non-breathing interval exceeds about 20 seconds.

Figure 14A:
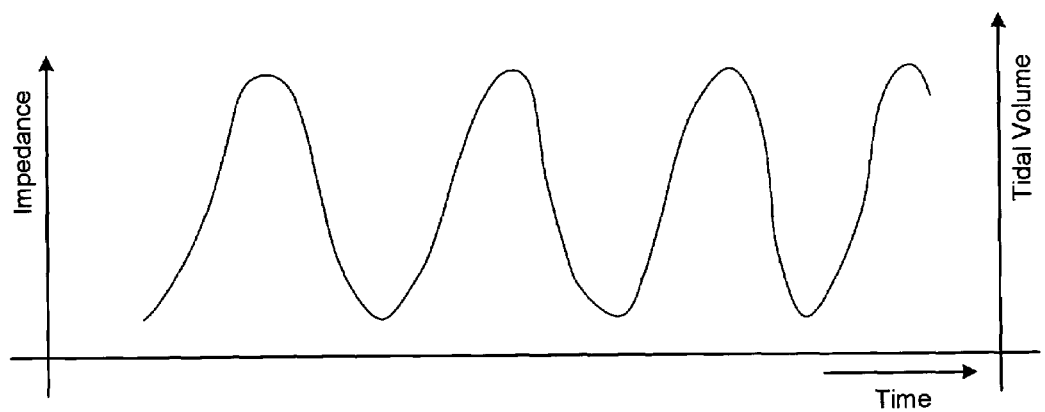
FIGS. 14A-14B are graphs of tidal volume derived from transthoracic impedance measurements according to embodiments of the invention.
Figure 14B:
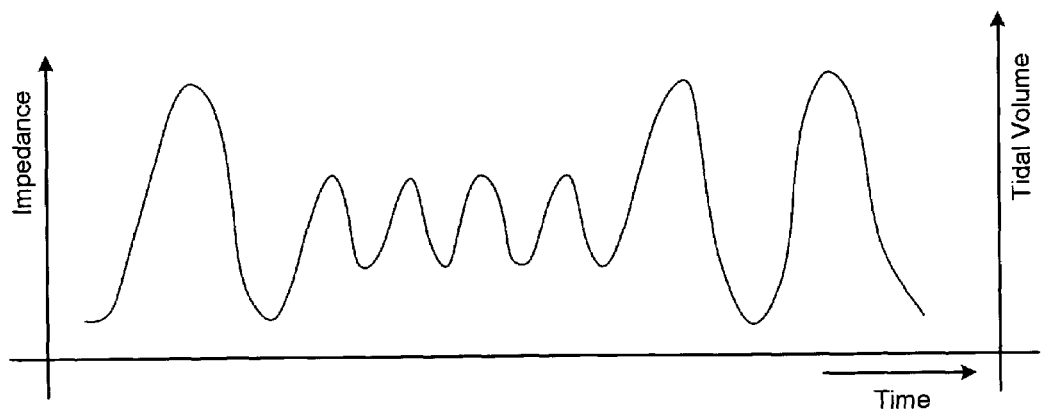

Hypopnea is a condition of disordered breathing characterized by abnormally shallow breathing. FIGS. 14A-B are graphs of tidal volume derived from transthoracic impedance measurements. The graphs compare the tidal volume of a normal breathing cycle to the tidal volume of a hypopnea episode. FIG. 14A illustrates normal respiration tidal volume and rate. As shown in FIG. 14B, hypopnea involves a period of abnormally shallow respiration.

According to an embodiment of the invention, hypopnea is detected by comparing a patient's respiratory tidal volume to a hypopnea tidal volume threshold. The tidal volume for each respiration cycle is derived from transthoracic impedance measurements acquired in the manner described above. The hypopnea tidal volume threshold may be established using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

Figure 15:
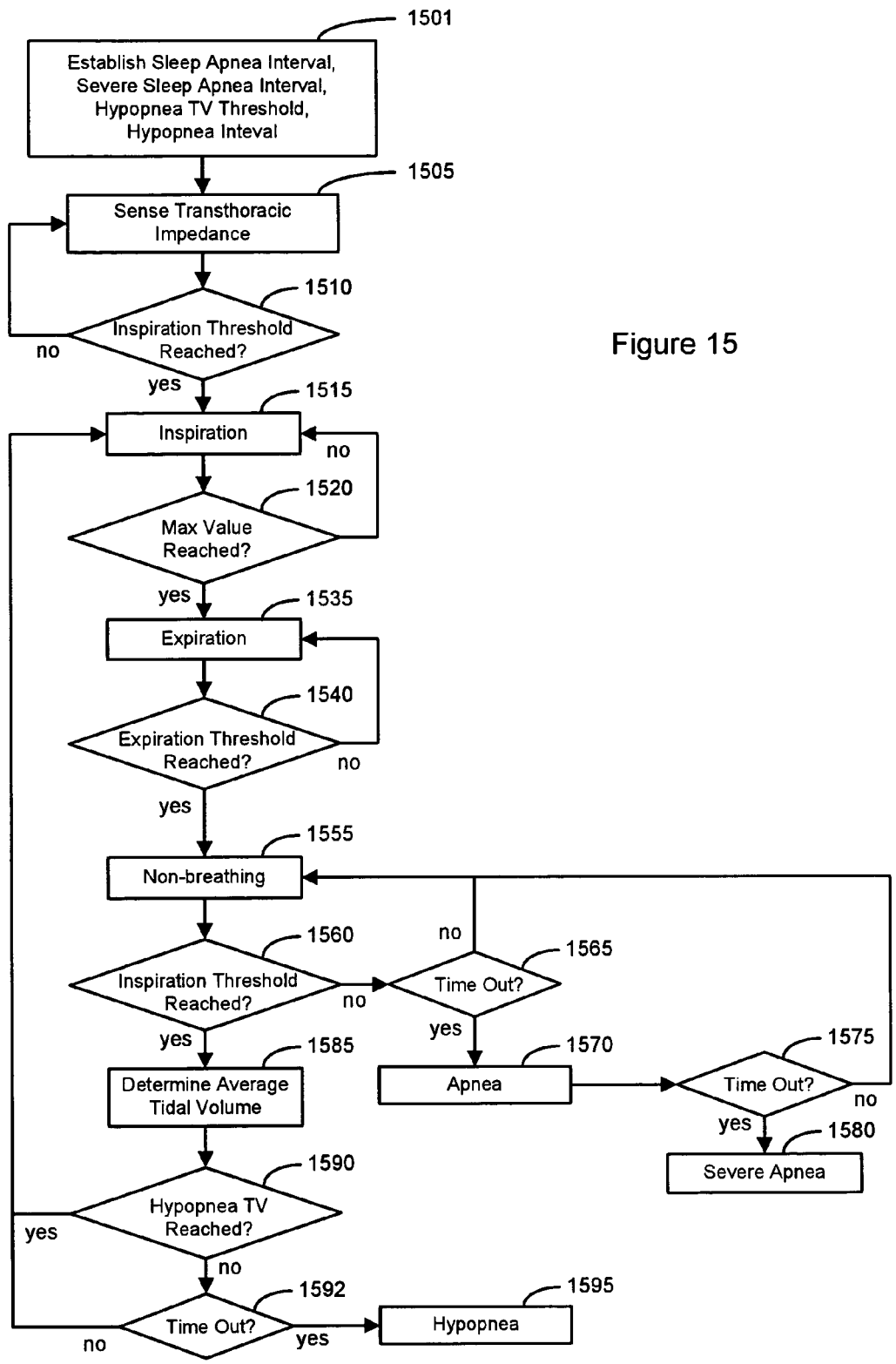
FIG. 15 is a flow graph illustrating a method of apnea and hypopnea detection according to embodiments of the invention.

FIG. 15 is a flow graph illustrating a method of apnea and/or hypopnea detection according to embodiments of the invention. Various parameters are established 1501 before analyzing the patient's respiration for disordered breathing episodes, including, for example, inspiration and expiration thresholds, sleep apnea interval, severe sleep apnea interval, and hypopnea tidal volume threshold.

The patient's transthoracic impedance is measured 1505 as described in more detail above. If the transthoracic impedance exceeds 1510 the inspiration threshold, the beginning of an inspiration interval is detected 1515. If the transthoracic impedance remains below 1510 the inspiration threshold, then the impedance signal is checked 1505 periodically until inspiration 1515 occurs.

During the inspiration interval, the patient's transthoracic impedance is monitored until a maximum value of the transthoracic impedance is detected 1520. Detection of the maximum value signals an end of the inspiration period and a beginning of an expiration period 1535.

The expiration interval is characterized by decreasing transthoracic impedance. When the transthoracic impedance falls below 1540 the expiration threshold, a non-breathing interval is detected 1555.

If the transthoracic impedance does not exceed 1560 the inspiration threshold within a first predetermined interval 1565, denoted the sleep apnea interval, then a condition of sleep apnea is detected 1570. Severe sleep apnea is detected 1580 if the non-breathing period extends beyond a second predetermined interval 1575, denoted the severe sleep apnea interval.

When the transthoracic impedance exceeds 1560 the inspiration threshold, the tidal volume from the peak-to-peak transthoracic impedance is calculated, along with a moving average of past tidal volumes 1585. The peak-to-peak transthoracic impedance provides a value proportional to the tidal volume of the respiration cycle. This value is compared 1590 to a hypopnea tidal volume threshold. If the peak-to-peak transthoracic impedance is consistent with 1590 the hypopnea tidal volume threshold for a predetermined time 1592, then a hypopnea cycle is detected 1595.

Additional sensors, such as motion sensors and/or posture sensors, may be used to confirm or verify the detection of a sleep apnea or hypopnea episode. The additional sensors may be employed to prevent false or missed detections of sleep apnea/hypopnea due to posture and/or motion related artifacts.

Another embodiment of the invention involves classifying respiration patterns as disordered breathing episodes based on the breath intervals and/or tidal volumes of one or more respiration cycles within the respiration patterns. According to this embodiment, the duration and tidal volumes associated with a respiration pattern are compared to duration and tidal volume thresholds. The respiration pattern is detected as a disordered breathing episode based on the comparison.

Figure 16:
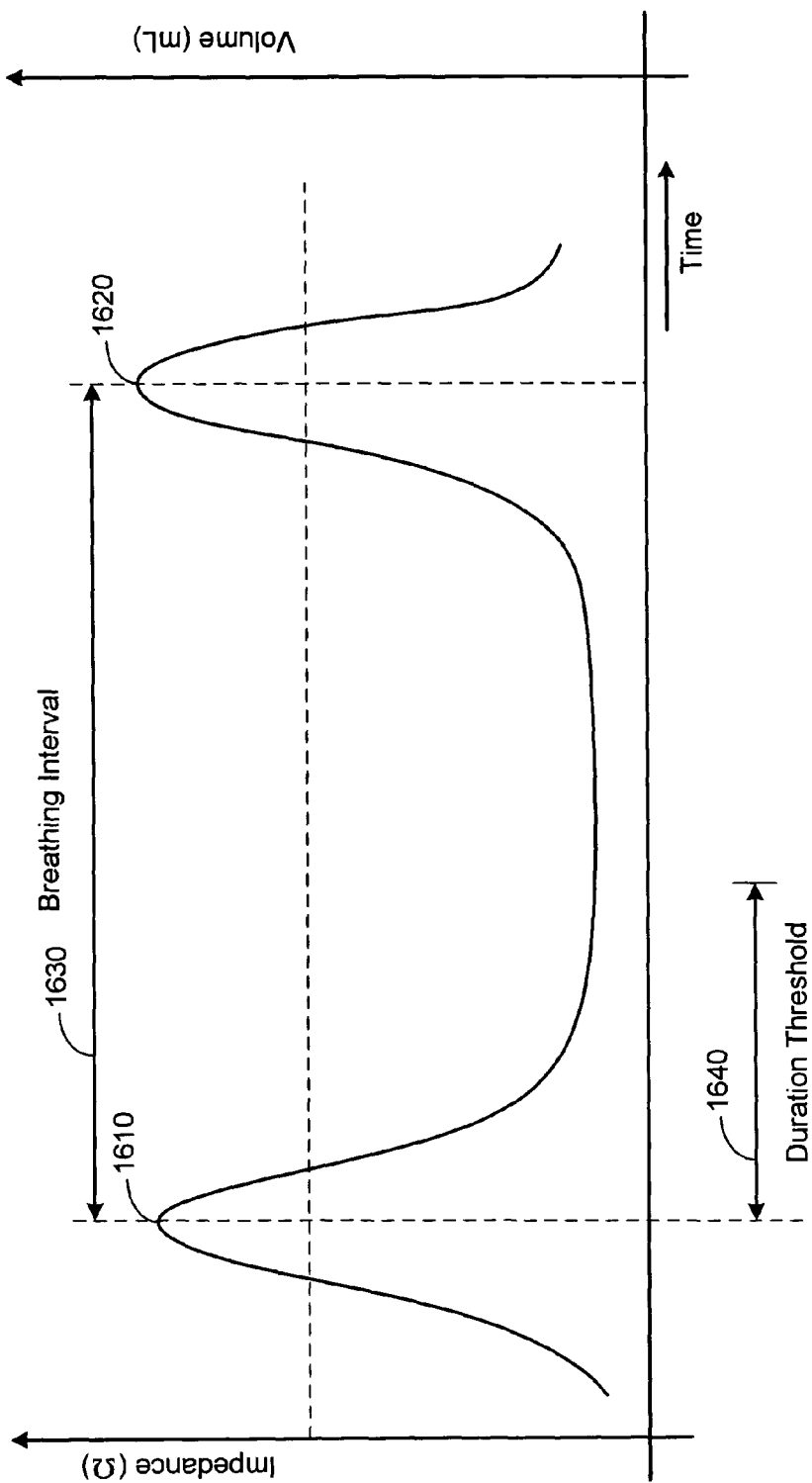
FIG. 16 is a graph illustrating a breathing interval according to embodiments of the invention.

According to principles of the invention, a breath interval 1630 is established for each respiration cycle. A breath interval represents the interval of time between successive breaths, as illustrated in FIG. 16. A breath interval 1630 may be defined in a variety of ways, for example, as the interval of time between successive maxima 1610, 1620 of the impedance signal waveform.

Detection of disordered breathing, in accordance with methods of the invention, involves the establishment of a duration threshold and a tidal volume threshold. If a breath interval exceeds the duration threshold, an apnea event is detected. Detection of sleep apnea, in accordance with this embodiment, is illustrated in the graph of FIG. 16. Apnea represents a period of non-breathing. A breath interval 1630 exceeding a duration threshold 1640, comprises an apnea episode.

Hypopnea may be detected using the duration threshold and tidal volume threshold. A hypopnea event represents a period of shallow breathing. Each respiration cycle in a hypopnea event is characterized by a tidal volume less than the tidal volume threshold. Further, the hypopnea event involves a period of shallow breathing greater than the duration threshold.

Figure 17:
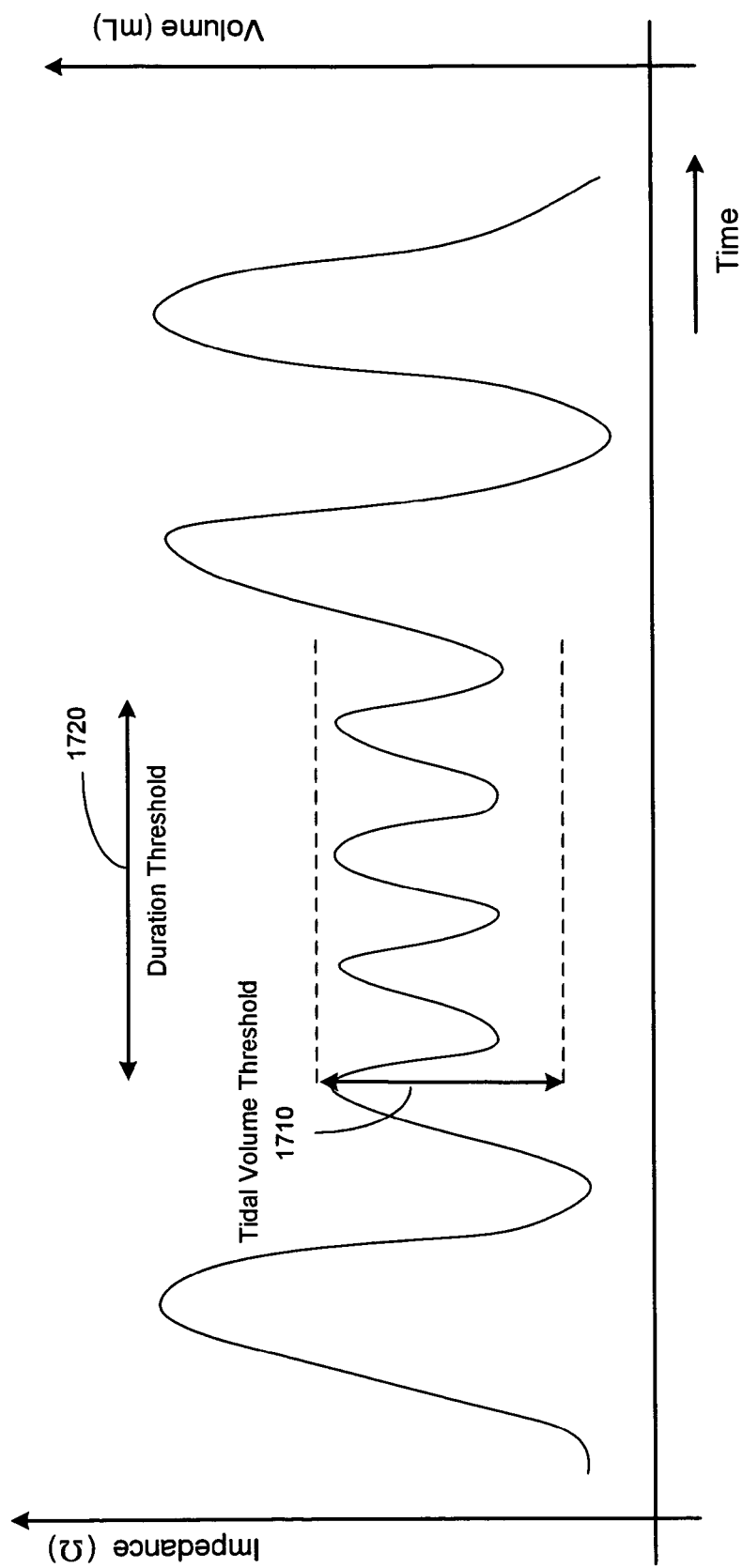
FIG. 17 is a graph illustrating a hypopnea detection approach in accordance with embodiments of the invention.

A hypopnea detection approach, in accordance with embodiments of the invention, is illustrated in FIG. 17. Shallow breathing is detected when the tidal volume of one or more breaths is below a tidal volume threshold 1710. If the shallow breathing continues for an interval greater than a duration threshold 1720, then the breathing pattern represented by the sequence of shallow respiration cycles, is classified as a hypopnea event.

Figure 18A:
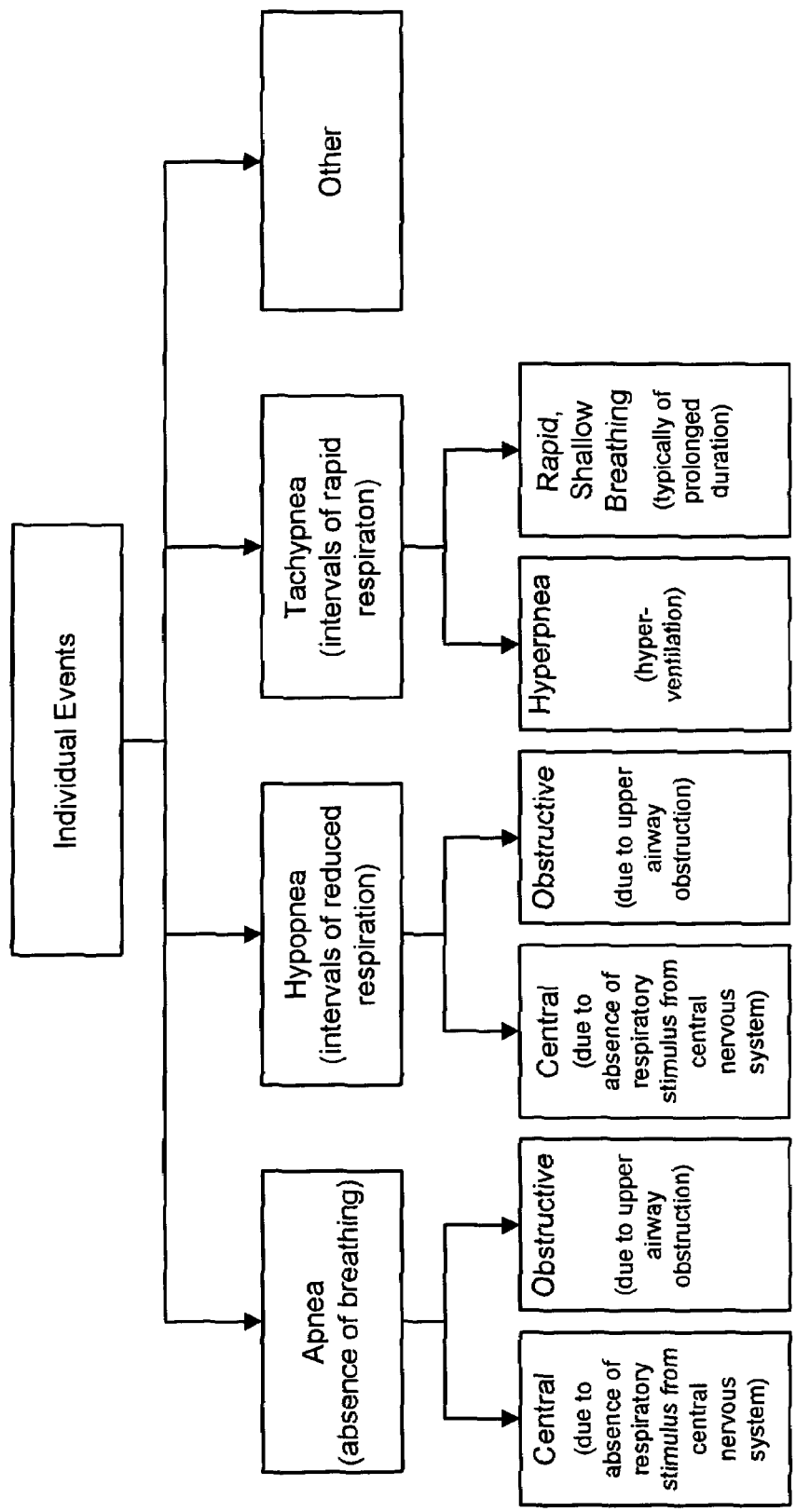
FIGS. 18A-18B are charts illustrating disordered breathing events that can be addressed in accordance with embodiments of the invention.
Figure 18B:
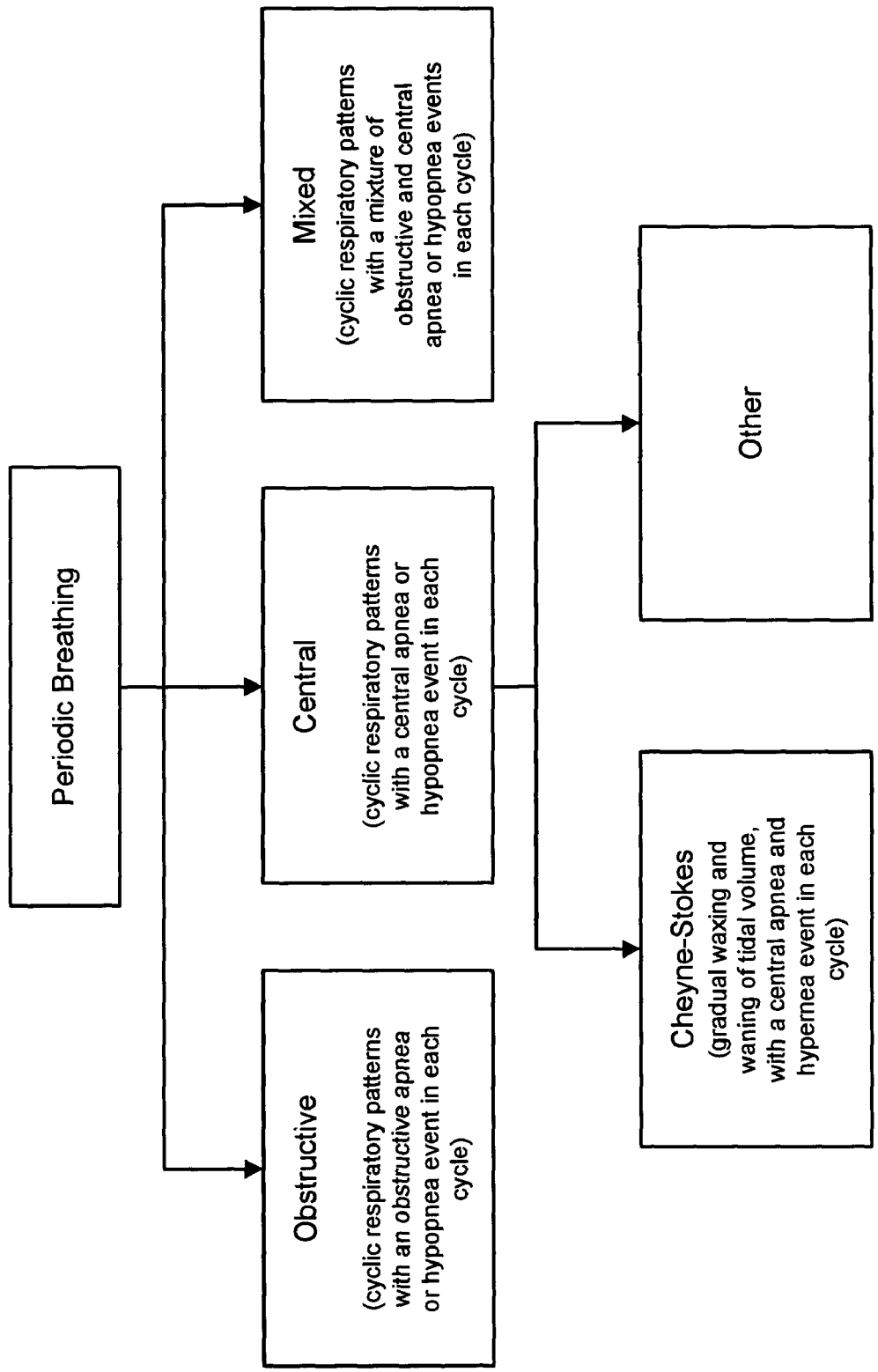

FIGS. 18A and 18B provide charts illustrating classification of individual disordered breathing events and series of periodically recurring disordered breathing events, respectively. As illustrated in FIG. 18A, individual disordered breathing events may be grouped into apnea, hypopnea, tachypnea and other disordered breathing events. Apnea events are characterized by an absence of breathing. Intervals of reduced respiration are classified as hypopnea events. Tachypnea events include intervals of rapid respiration characterized by an elevated respiration rate.

As illustrated in FIG. 18A, apnea and hypopnea events may be further subdivided as either central events, caused either by central nervous system dysfunction, or obstructive events, caused by upper airway obstruction. A tachypnea event may be further classified as a hyperpnea event, represented by hyperventilation, i.e., rapid deep breathing. A tachypnea event may alternatively be classified as rapid shallow breathing, typically of prolonged duration.

FIG. 18B illustrates classification of combinations of periodically recurring disordered breathing events. Periodic breathing may be classified as obstructive, central or mixed. Obstructive periodic breathing is characterized by cyclic respiratory patterns with an obstructive apnea or hypopnea event in each cycle. In central periodic breathing, the cyclic respiratory patterns include a central apnea or hypopnea event in each cycle. Periodic breathing may also be of mixed origin. In this case, cyclic respiratory patterns have a mixture of obstructive and central apnea events in each cycle. Cheyne-Stokes is a particular type of periodic breathing characterized by a gradual waxing and waning or tidal volume and having a central apnea and hyperpnea event in each cycle. Other manifestations of periodic breathing are also possible.

As illustrated in FIGS. 18C-G, a respiration pattern detected as a disordered breathing episode may include only an apnea respiration cycle 1810 (FIG. 18C), only hypopnea respiration cycles 1850 (FIG. 18F), or a mixture of hypopnea and apnea respiration cycles 1820 (FIG. 18D), 1830 (FIG. 18E), 1860 (FIG. 18G). A disordered breathing event 1820 may begin with an apnea respiration cycle and end with one or more hypopnea cycles. In another pattern, the disordered breathing event 1830 may begin with hypopnea cycles and end with an apnea cycle. In yet another pattern, a disordered breathing event 1860 may begin and end with hypopnea cycles with an apnea cycle in between the hypopnea cycles.

Figure 19:
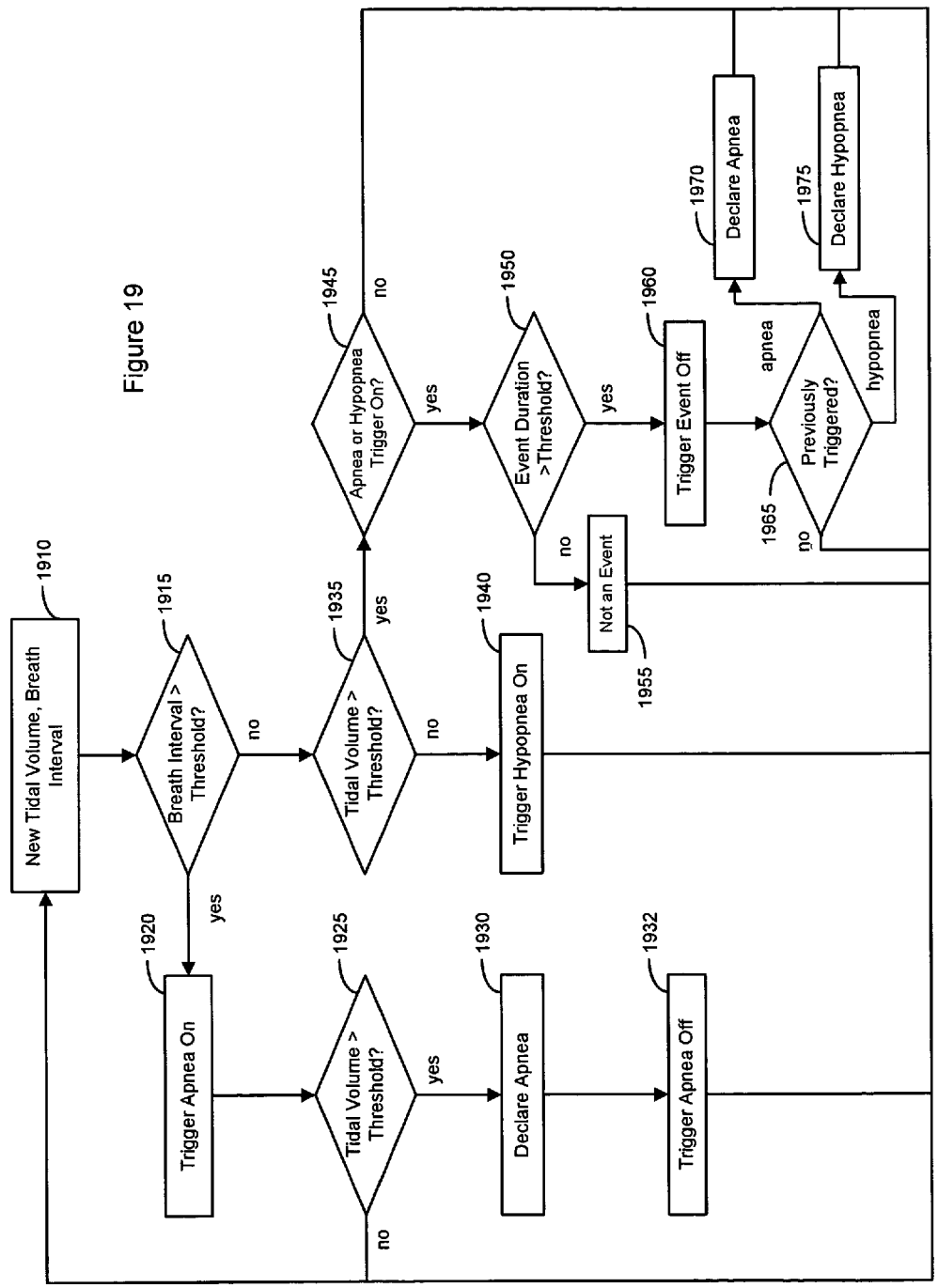
FIG. 19 is a flow graph of a method for detecting disordered breathing by classifying breathing patterns in accordance with embodiments of the invention.

FIG. 19 is a flow graph of a method for detecting disordered breathing by classifying breathing patterns using breath intervals in conjunction with tidal volume and duration thresholds as previously described above. In this example, a duration threshold and a tidal volume threshold are established for determining both apnea and hypopnea breath intervals. An apnea episode is detected if the breath interval exceeds the duration threshold. A hypopnea episode is detected if the tidal volume of successive breaths remains less than the tidal volume threshold for a period in excess of the duration threshold. Mixed apnea/hypopnea episodes may also occur. In these cases, the period of disordered breathing is characterized by shallow breaths or non-breathing intervals. During the mixed apnea/hypopnea episodes, the tidal volume of each breath remains less than the tidal volume threshold for a period exceeding the duration threshold.

Transthoracic impedance is sensed and used to determine the patient's respiration cycles. Each breath 1910 is characterized by a breath interval, defined by the interval of time between two impedance signal maxima, and a tidal volume (TV).

If a breath interval exceeds 1915 the duration threshold, then the respiration pattern is consistent with an apnea event, and an apnea event trigger is turned on 1920. If the tidal volume of the breath interval exceeds 1925 the tidal volume threshold, then the breathing pattern is characterized by two respiration cycles of normal volume separated by a non-breathing interval. This pattern represents a purely apneic disordered breathing event, and apnea is detected 1930. Because the final breath of the breath interval was normal, the apnea event trigger is turned off 1932, signaling the end of the disordered breathing episode. However, if the tidal volume of the breath interval does not exceed 1925 the tidal volume threshold, the disordered breathing period is continuing and the next breath is checked 1910.

If the breath interval does not exceed 1915 the duration threshold, then the tidal volume of the breath is checked 1935. If the tidal volume does not exceed 1935 the tidal volume threshold, the breathing pattern is consistent with a hypopnea cycle and a hypopnea event trigger is set on 1940. If the tidal volume exceeds the tidal volume threshold, then the breath is normal.

If a period of disordered breathing is in progress, detection of a normal breath signals the end of the disordered breathing. If disordered breathing was previously detected 1945, and if the disordered breathing event duration has not exceeded 1950 the duration threshold, and the current breath is normal, then no disordered breathing event is detected 1955. If disordered breathing was previously detected 1945, and if the disordered breathing event duration has extended for a period of time exceeding 1950 the duration threshold, and the current breath is normal, then the disordered breathing trigger is turned off 1960. In this situation, the duration of the disordered breathing episode was of sufficient duration to be classified as a disordered breathing episode. If an apnea event was previously triggered 1965, then an apnea event is declared 1970. If a hypopnea was previously triggered 1965, then a hypopnea event is declared 1975.

Figure 20:
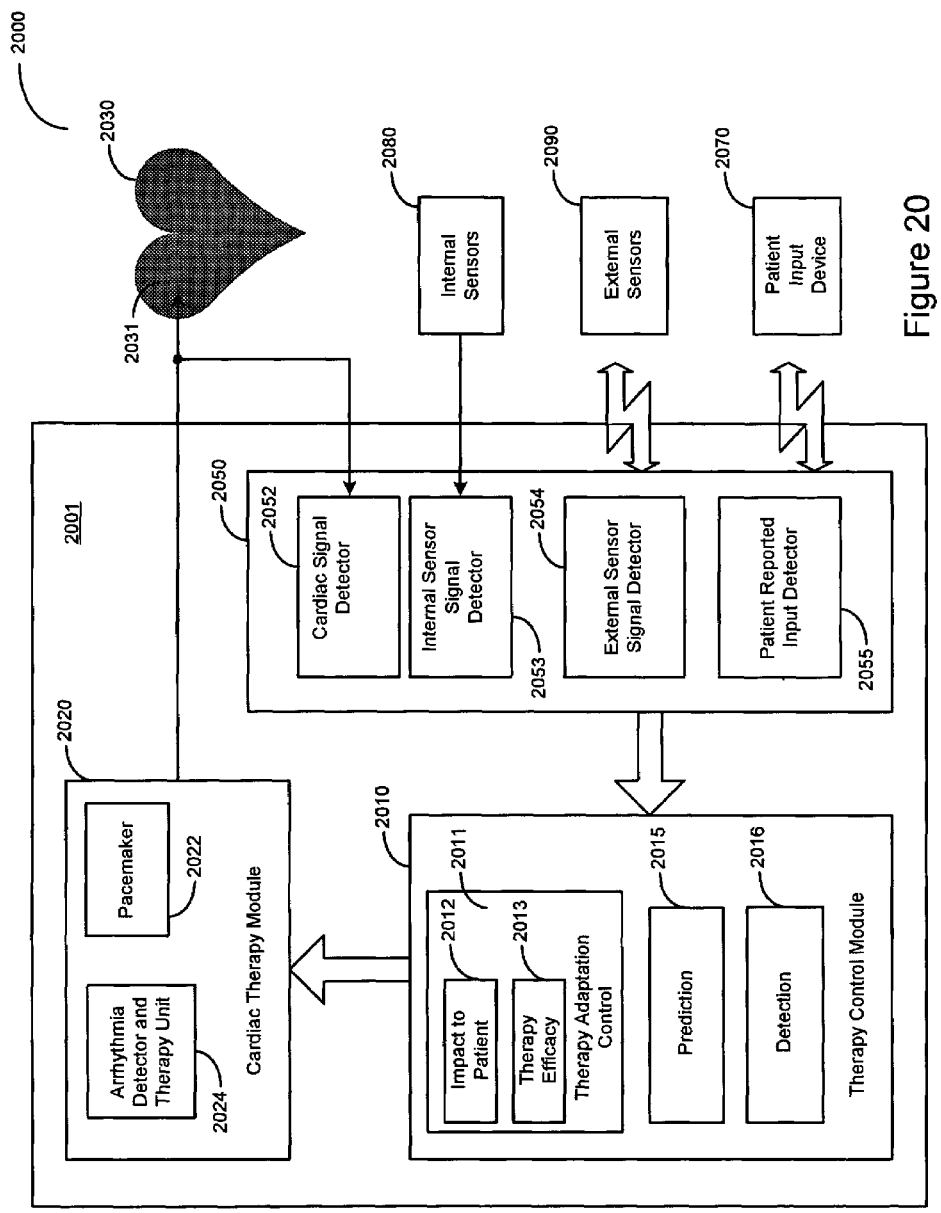
FIG. 20 is a block diagram illustrating a system for adapting a therapy to mitigate disordered breathing based on therapy efficacy and minimal impact to the patient.

FIG. 20 illustrates a block diagram of a system 2000 that may be used to provide disordered breathing therapy in accordance with embodiments of the invention. According to various embodiments, therapy to mitigate disordered breathing may be triggered by a prediction of disordered breathing. The therapy may be adapted based on therapy efficacy and/or the impact of the therapy on the patient.

In one example implementation, a disordered breathing therapy control system 2010 is incorporated within a cardiac rhythm management system 2001 capable of providing therapeutic electrical stimulation to a patient's heart. The cardiac rhythm management system 2001 may include, for example, a cardiac therapy module 2020, including a pacemaker 2022, and an arrhythmia detector/therapy unit 2024. The cardiac rhythm management system 2001 is coupled to a lead system having electrodes 2031 electrically coupling the patient's heart 2030 to the cardiac rhythm management system 2001.

The cardiac rhythm management system 2001 may include circuitry 2050 used to detect signals from patient-internal sensors such as the implanted cardiac electrodes 2031, and other patient-internal sensors 2080, including, for example, any of the patient-internal sensors listed in Table 1. The cardiac electrodes 2031 and the patient-internal sensors 2080 are coupled to a cardiac signal detector 2052 and a patient-internal sensor signal detector 2053, respectively. The cardiac electrodes 2031 and patient-internal sensors 2080 may be coupled to the detector system 2050 through conducting leads as shown, or through a wireless connection, for example.

The cardiac rhythm management system 2001 may also include circuitry 2054 for detecting signals from patient-external sensors 2090 positioned outside the patient's body. The patient-external sensors 2090 may be coupled to the detection circuitry 2054 through a wireless link. In addition, the patient may input information relevant to disordered breathing detection or therapy using a patient input device 2070. Signals representing patient-reported data may be wirelessly coupled to patient-input detection circuitry 2055.

The cardiac therapy module 2020 receives cardiac signals from the implanted cardiac electrodes 2031 and analyzes the cardiac signals to determine an appropriate cardiac therapy. The cardiac therapy may include pacing therapy controlled by the pacemaker 2022 to treat cardiac rhythms that are too slow. For example, the pacemaker 2022 may control the delivery of periodic low energy pacing pulses to one or more of the heart chambers through the cardiac electrodes 2031 to ensure that the periodic contractions of the heart are maintained at a hemodynamically sufficient rate.

The cardiac therapy may also include therapy to terminate tachyarrhythmia, wherein the heart rate is too fast. The arrhythmia detector/therapy unit 2024 detects and treats episodes of tachyarrhythmia, including tachycardia and/or fibrillation. The arrhythmia detector/therapy unit 2024 recognizes cardiac signal waveforms indicative of tachyarrhythmia and controls the delivery of high energy stimulations to the heart 2030 through the implanted electrodes 2031 to terminate the arrhythmia.

A disordered breathing control module 2010 incorporated within the cardiac rhythm management system 2001 includes a prediction engine 2015, disordered breathing detection circuitry 2016, and a therapy adaptation control module 2011. The signal detection circuitry 2050 detects conditions relevant to disordered breathing prediction, detection, and therapy control used by to the disordered breathing control module 2010.

A prediction of disordered breathing by the disordered breathing prediction engine 2015 may be used to trigger cardiac pacing therapy delivered by the cardiac therapy module 2020 to mitigate or prevent the disordered breathing. In one illustrative therapy regimen, pacing to mitigate disordered breathing may include pacing at a rate exceeding an intrinsic rate. In another example, the pacing pulses may be delivered at a rate above the patient's normal sleep rate. The pacing may involve any or all of the heart chambers, for example, right and left atria and right and left ventricles. The pacing may also involve bi-atrial, bi-ventricular, or multi-site pacing. In bi-atrial pacing, the pacing pulses may be delivered to left and right atria simultaneously, or according to other timing sequences. Bi-ventricular pacing may be accomplished by the simultaneous or otherwise timed application of pacing pulses to the left and right ventricles of the heart.

In other embodiments, adapting the cardiac electrical therapy to mitigate disordered breathing may involve initiating a particular pacing regimen or switching from one pacing mode to another pacing mode. In one example, the cardiac pacing regimen may be switched from a dual-chamber pacing mode to a bi-ventricular or other resynchronization mode. In other examples, the pacing mode may be switched to a pacing mode that promotes atrial pacing, or promotes consistent ventricular pacing. In yet another example, the cardiac electrical therapy may involve initiating multi-site electrical stimulation to the heart or changing from one electrical stimulation site to another. The pacing mode may be switched from single chamber to multiple chambers, or the reverse. For example, a bi-ventricular mode may be switched to a left ventricular mode only. Alternatively, a single chamber mode, e.g., LV or RV, may be switched to a bi-ventricular mode. Other therapy regimens, involving, e.g., various pacing modes, pacing sites, or non-excitatory electrical stimulations, are possible in connection with providing cardiac electrical therapy for disordered breathing. The type of cardiac electrical therapy beneficial to a patient is highly patient specific and may be determined based on the responses of a particular patient.

The patient conditions detected by the signal detector system 2050 are used to adapt disordered breathing therapy with respect to providing a more effective therapy, or to decrease the negative impact of the therapy on the patient, or both. A therapy adaptation control module 2011 coupled to the therapy module includes components for assessing patient impact 2012 and therapy efficacy 2013 implemented according to the previously described methods. The therapy adaptation control module 2011 is coupled to the therapy control module 2020 and provides control signals to the therapy module for adapting the therapy.

Figure 21:
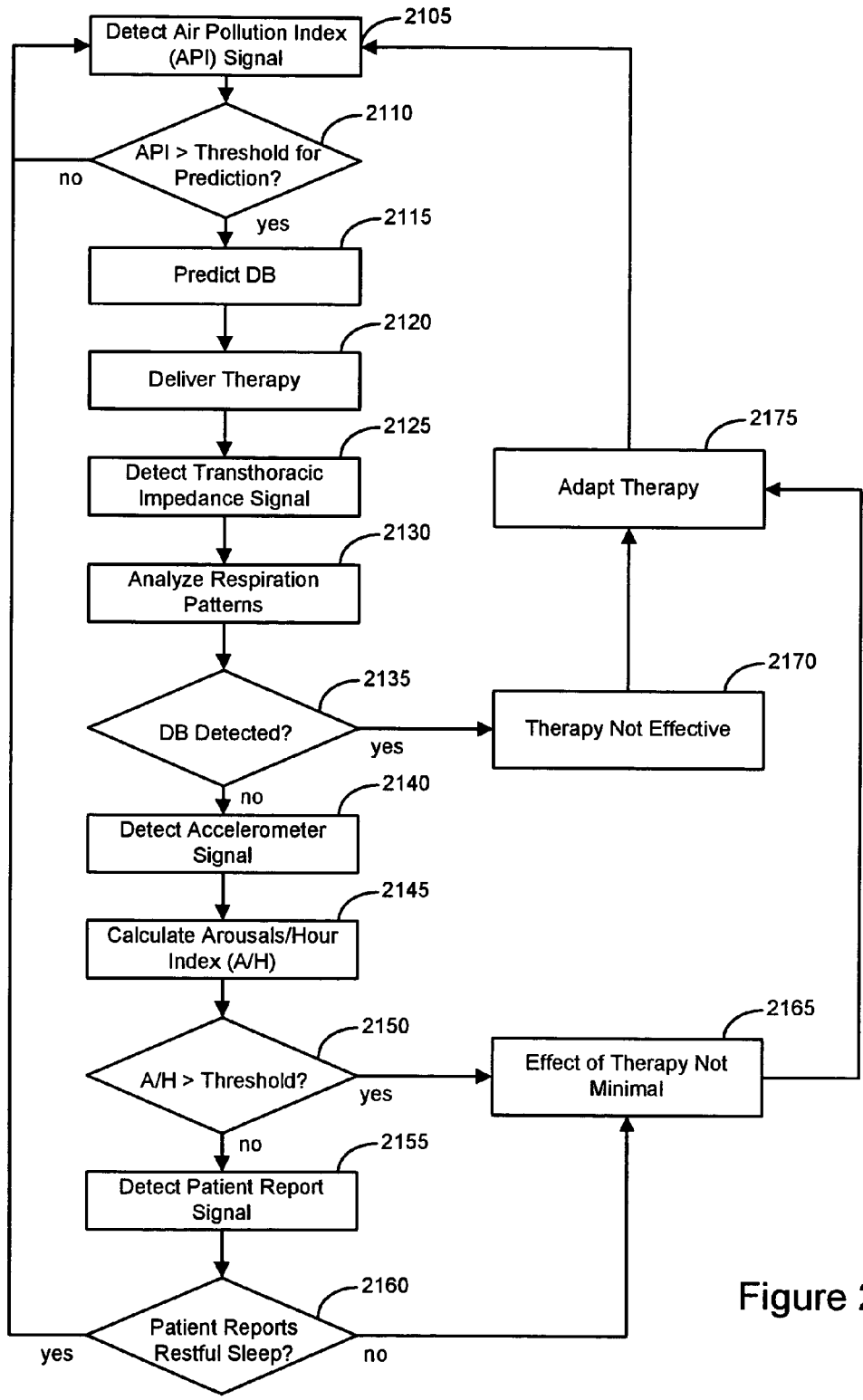
FIG. 21 is a flow graph of a method of adapting a therapy for disordered breathing using disordered breathing detection and sleep quality assessment.

FIG. 21 is a flow graph illustrating a method of providing cardiac pacing therapy for disordered breathing in accordance with embodiments of the invention. The cardiac pacing therapy is triggered by a prediction of disordered breathing.

In this example, disordered breathing is predicted based on an air pollution index obtained from an internet accessible server. Therapy efficacy is assessed by analyzing respiration patterns detected using a transthoracic impedance sensor to detect episodes of disordered breathing. The impact of the therapy on the patient's sleep is analyzed by determining the number of arousals per hour experienced by the patient.

As illustrated in FIG. 21, an air pollution index is detected 2105, for example, by accessing an internet-connected website. If the air pollution index exceeds a selected threshold 2110, then disordered breathing is predicted 2115. The air pollution index threshold may be selected, for example, from data collected over time from the patient. If disordered breathing is predicted 2115, therapy to mitigate the disordered breathing, e.g., cardiac pacing therapy, is delivered 2120 to the patient. The pacing may involve, for example, pacing at a predetermined amount over the intrinsic rate or the current pacing rate. The predetermined amount may initially be a nominal amount, such as 15 bpm over the intrinsic or the current rate. The pacing rate may be modified to increase the efficacy of the therapy or to reduce the impact of the therapy on the patient.

A transthoracic impedance signal is sensed 2125 and used to analyze 2130 respiration patterns associated with disordered breathing. If disordered breathing is detected 2135, then the delivered therapy may not have been effective 2170. If therapy is found to be ineffective, the therapy may be adapted 2175.

In one embodiment, if the frequency, duration, or severity of the disordered breathing episodes is not mitigated following therapy delivery, the therapy may be determined to be ineffective and the pacing rate may be adapted to a higher pacing rate. Severity of disordered breathing events may be assessed, for example, as a percentage decrease in tidal volume from the recent average or baseline tidal volume.

Disordered breathing time duration thresholds may be defined to trigger an disordered breathing episode. For example, a disordered breathing episode may be declared if the patient's tidal volume falls below an apnea or hypopnea tidal volume threshold for a period exceeding a disordered breathing duration threshold such as about 10 seconds. A severe disordered breathing episode may be declared when the patient's tidal volume falls below an apnea or hypopnea tidal volume threshold for a period exceeding a severe disordered breathing duration threshold, e.g., about 60 seconds. If a severe apnea episode is detected, the severe apnea episode may trigger pacing at a high rate to arouse the patient and terminate the apnea. A pacing rate upper limit may be employed to prevent the pacing rate from becoming too high.

In one embodiment, if the therapy is determined to be effective, the pacing rate may be gradually decreased to reduce the risk of arousal, to avoid unnecessary stress on the heart, and to prolong battery life.

If the disordered breathing therapy is determined to be effective 2135, the impact of the therapy on the patient is assessed. The patient's sleep quality may be determined by analyzing patient activity using an accelerometer, for example. Additional sensors may also be used to provide more sensitive arousal detection. The accelerometer signal is sensed 2140 and used to determine 2145 the number of arousals per hour (A/H) experienced by the patient. If the number of arousals per hour is greater 2150 than a threshold value, then the therapy may be arousing the patient from sleep. In this situation, the impact of the therapy is not minimal 2165, and the therapy may be adapted 2175. The impact of the therapy may be further assessed using patient-reported input 2155. If the patient reports that sleep is not restful 2160, then the therapy regimen may be adapted 2175.

Although a number of the examples of disordered breathing therapy provided above involve types of disordered breathing that generally occur while a person is asleep, disordered breathing may also occur while a person is awake. While the methods, devices, and systems of the invention described herein are particularly well-suited for providing sleep-disordered breathing therapy, the principles of the invention are also applicable to provided therapy for disordered breathing episodes that occur while the patient is awake. Waking disordered breathing is frequently associated with compromised cardiopulmonary function caused by congestive heart failure. Examples of the types of disordered breathing that may occur while a person is awake include, for example, periodic breathing and Cheyne-Stokes respiration. Cheyne-Stokes respiration particularly affects patients who have heart problems, such as congestive heart failure, or nervous disorders, such as those caused by a stroke.

The following commonly owned U.S. Patents Applications, some of which have been identified above, are hereby incorporated by reference in their respective entireties: U.S. patent application Ser. No. 10/309,771, filed Dec. 4, 2002, now U.S. Pat. No. 7,189,204, U.S. patent application Ser. No. 10/309,770, filed Dec. 4, 2002, now U.S. Pat. No. 7,252,640, U.S. patent application Ser. No. 10/642,998 entitled "Sleep Quality Data Collection and Evaluation," now U.S. Publication No. 2005/0042589, and concurrently filed with this patent application, U.S. patent application Ser. No. 10/643,203 entitled "Adaptive Therapy for Disordered Breathing," now U.S. Publication No. 2005/0039745 and filed concurrently with this patent application, U.S. patent application Ser. No. 10/643,006 entitled "Sleep State Classification," now U.S. Publication No. 2005/0043652, and filed concurrently with this patent application, and U.S. patent application Ser. No. 10/643,016 entitled "Prediction of Disordered Breathing," now U.S. Pat. No. 7,396,333, and filed concurrently with this patent application.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of providing disordered breathing therapy to a patient, comprising:

detecting one or more conditions associated with disordered breathing;

predicting disordered breathing based on the one or more detected conditions using at least a first disordered breathing prediction criteria set;

estimating an accuracy of the first disordered breathing prediction criteria set; and delivering cardiac electrical stimulation therapy to mitigate the predicted disordered breathing, wherein at least one of detecting, predicting, and delivering is performed at least in part implantably.

2. The method of claim 1, wherein at least two of detecting, predicting, and delivering are performed at least in part implantably.

3. The method of claim 1, wherein each of detecting, predicting, and delivering is performed at least in part implantably.

4. The method of claim 1, wherein detecting the one or more conditions comprises detecting a physiological condition.

5. The method of claim 1, wherein detecting the one or more conditions comprises detecting a respiratory system condition.

6. The method of claim 1, wherein detecting the one or more conditions comprises detecting a cardiovascular system condition.

7. The method of claim 1, wherein detecting the one or more conditions comprises detecting a nervous system condition.

8. The method of claim 1, wherein detecting the one or more conditions comprises detecting a blood chemistry condition.

9. The method of claim 1, wherein detecting the one or more conditions comprises detecting a muscle system condition.

10. The method of claim 1, wherein detecting the one or more conditions comprises detecting a non-physiological condition.

11. The method of claim 1, wherein detecting the one or more conditions comprises detecting an environmental condition.

12. The method of claim 1, wherein detecting the one or more conditions comprises detecting a contextual condition.

13. The method of claim 1, wherein detecting the one or more conditions comprises detecting a historical patient condition.

14. The method of claim 1, wherein detecting the one or more conditions comprises detecting a body-related condition.

15. The method of claim 1, wherein detecting the one or more conditions comprises detecting a condition used to verify the prediction of disordered breathing.

16. The method of claim 1, wherein detecting the one or more conditions comprises detecting a condition predisposing the patient to disordered breathing.

17. The method of claim 16, wherein detecting the predisposing condition comprises detecting a condition associated with an increased likelihood of disordered breathing.

18. The method of claim 1, wherein predicting the disordered breathing comprises predicting the disordered breathing will occur within a selected time interval from a time of the disordered breathing prediction.

19. The method of claim 18, wherein the selected time interval comprises about an 8 hour period following the time of the disordered breathing prediction.

20. The method of claim 18, wherein the selected time interval comprises a next sleep time following the time of the disordered breathing prediction.

21. The method of claim 18, wherein the selected time interval comprises about a 300 second period following the time of the disordered breathing prediction.

22. The method of claim 1, wherein detecting the one or more conditions comprises detecting a precursor condition to disordered breathing.

23. The method of claim 22, wherein detecting the precursor condition comprises detecting a condition associated with an impending onset of disordered breathing.

24. The method of claim 1, wherein predicting the disordered breathing comprises performing a real-time prediction of disordered breathing.

25. The method of claim 1, wherein predicting the disordered breathing comprises:
comparing the one or more detected conditions to one or more sets of prediction criteria associated with disordered breathing, the one or more sets including the first disordered breathing prediction criteria set; and
predicting the disordered breathing based on the comparison.

26. The method of claim 1, wherein predicting the disordered breathing comprises:
comparing the one or more detected conditions to one or more sets of disordered breathing threshold criteria, the one or more sets including the first disordered breathing prediction criteria set; and
predicting the disordered breathing based on the comparison.

27. The method of claim 1, wherein predicting the disordered breathing comprises:
comparing a relationship between the one or more detected conditions to one or more sets of disordered breathing relationship criteria, the one or more sets including the first disordered breathing prediction criteria set; and
predicting disordered breathing based on the comparison.

28. The method of claim 1, wherein predicting the disordered breathing comprises:
computing an estimated probability that disordered breathing will occur based on the conditions;
comparing the estimated probability to a threshold probability associated with an onset of disordered breathing; and
predicting the disordered breathing based on the comparison.

29. The method of claim 28, wherein computing an estimated probability comprises computing a composite estimated probability score.

30. The method of claim 1, further comprising establishing one or more sets of disordered breathing prediction criteria, including the first disordered breathing prediction criteria set.

31. The method of claim 30, wherein establishing the one or more sets of disordered breathing prediction criteria comprises establishing the one or more sets of disordered breathing prediction criteria based on the detected conditions.

32. The method of claim 30, wherein establishing the one or more sets of disordered breathing prediction criteria comprises establishing the one or more sets of disordered breathing prediction criteria based on clinical data.

33. The method of claim 1, further comprising:
providing one or more sets of disordered breathing prediction criteria, including the first disordered breathing prediction criteria set; and
adjusting at least one of the one or more disordered breathing prediction criteria sets using the detected conditions.

34. The method of claim 33, wherein the adjusting is performed at least in part implantably.

35. The method of claim 33, wherein the adjusting comprises:
calculating an estimated accuracy for a particular set of prediction criteria; and
adjusting the particular set of prediction criteria based on the estimated accuracy.

36. The method of claim 33, wherein the adjusting comprises:
calculated an estimated sensitivity for a particular set of prediction criteria; and adjusting the particular set of prediction criteria based on the estimated sensitivity.

37. The method of claim 33, wherein providing the one or more sets of prediction criteria comprises forming a particular set of prediction criteria based on data based on the one or more detected conditions.

38. The method of claim 33, wherein providing the one or more sets of prediction criteria comprises deleting a particular set of prediction criteria based on data based on the one or more detected conditions.

39. The method of claim 1, wherein delivering the cardiac electrical therapy to mitigate the predicted disordered breathing comprises delivering the cardiac electrical therapy to reduce a severity of the predicted disordered breathing.

40. The method of claim 1, wherein delivering the cardiac electrical therapy to mitigate the predicted disordered breathing comprises delivering the cardiac electrical therapy to prevent the predicted disordered breathing.

41. The method of claim 1, wherein delivering the electrical stimulation therapy comprises delivering cardiac pacing therapy.

42. The method of claim 1, wherein delivering the electrical stimulation therapy comprises delivering atrial pacing therapy.

43. The method of claim 1, wherein the delivering the therapy comprises delivering ventricular pacing therapy.

44. The method of claim 1, wherein delivering the cardiac electrical therapy comprises delivering multi-chamber therapy.

45. The method of claim 1, wherein delivering the cardiac electrical therapy comprises delivering multi-site therapy.

46. The method of claim 1, wherein delivering the cardiac electrical therapy comprises delivering non-excitatory therapy.

47. The method of claim 1, wherein delivering the therapy comprises delivering cardiac pacing therapy at a rate above an intrinsic rate.

48. The method of claim 1, wherein delivering the therapy comprises delivering cardiac pacing therapy at a rate above a normally programmed pacing rate.

49. A medical device, comprising:
a detector system configured to detect one or more conditions associated with disordered breathing of a patient;
a prediction engine coupled to the detector system and configured to predict disordered breathing based on the detected conditions using at least a first disordered breathing prediction criteria set, the prediction engine also being configured to estimate an accuracy of the first disordered breathing prediction criteria set; and
a therapy delivery system coupled to the prediction engine and the detector system and configured to deliver therapy to the patient to mitigate the predicted disordered breathing, wherein the prediction engine includes an implantable component.

50. The medical device of claim 49, wherein the therapy delivery system includes an implantable component.

51. The medical device of claim 49, wherein the therapy delivery system and the detector system include implantable components.

52. The medical device of claim 49, wherein the detector system comprises a patient-internal sensor.

53. The medical device of claim 49, wherein the detector system comprises a patient-external sensor.

54. The medical device of claim 49, wherein the detector system comprises a patient input device.

55. The medical device of claim 49, wherein the detector system comprises a sensor configured to sense a physiological condition.

56. The medical device of claim 49, wherein the detector system comprises a sensor configured to sense a contextual condition.

57. The medical device of claim 49, wherein the detector system is configured to include at least one wirelessly connected component.

58. The medical device of claim 49, wherein the prediction engine is configured to compare the one or more detected conditions to one or more sets of disordered breathing prediction criteria, including the first disordered breathing prediction criteria set, and to predict the disordered breathing based on the comparison.

59. The medical device of claim 49, wherein the prediction engine is configured to establish a particular set of prediction criteria based on the detected conditions.

60. The medical device of claim 49, wherein the prediction engine is configured to adjust a particular set of prediction criteria based on the detected conditions.

61. The medical device of claim 49, wherein the prediction engine is configured to perform real-time prediction of the disordered breathing.

62. The medical device of claim 49, further comprising a controller configured to adapt the therapy delivered to the patient.

63. The medical device of claim 62, wherein the controller is configured to adapt the therapy to reduce an impact of the therapy on the patient.

64. The medical device of claim 62, wherein the controller is configured to adapt the therapy to enhance therapy efficacy.

65. The medical device of claim 62, wherein the controller is configured to adapt the therapy to reduce therapy interaction.

66. The medical device of claim 62, wherein the controller is configured to adapt the therapy to extend device service life.

67. The medical device of claim 49, wherein the therapy delivery system is configured to deliver cardiac pacing therapy.

68. The medical device of claim 49, wherein the therapy delivery system is configured to deliver non-excitatory electrical stimulation.

69. A disordered breathing therapy system, comprising:
means for detecting one or more conditions associated with disordered breathing in a patient;
means for predicting disordered breathing based on the one or more detected conditions using at least a first disordered breathing prediction criteria set;
means for estimating an accuracy of the first disordered breathing prediction criteria set; and
means for delivering cardiac electrical therapy to mitigate the predicted disordered breathing, wherein at least one of the means for detecting, the means for predicting, and the means for delivering includes an implantable component.

* * * * *